(12) United States Patent
Stevens et al.

(10) Patent No.: US 7,384,966 B2
(45) Date of Patent: Jun. 10, 2008

(54) 2-ARYLBENZOTHIAZOLE DERIVATIVES

(75) Inventors: Malcolm Francis G. Stevens, Long Whatton (GB); Andrew David Westwell, Nottingham (GB); Tracey Dawn Poole, Chesterfield (GB); Geoffrey Wells, Hull (GB)

(73) Assignee: Pharminxo Limited, Abingdon (GB)

( * ) Notice: Subject to any disclaimer, the term of this patent is extended or adjusted under 35 U.S.C. 154(b) by 0 days.

(21) Appl. No.: 11/215,223

(22) Filed: Aug. 31, 2005

(65) Prior Publication Data

US 2006/0063816 A1    Mar. 23, 2006

Related U.S. Application Data

(60) Provisional application No. 60/605,715, filed on Aug. 31, 2004.

(51) Int. Cl.
*A61K 31/428* (2006.01)
*C07D 277/68* (2006.01)
*C07D 277/64* (2006.01)

(52) U.S. Cl. ..................... 514/367; 548/152

(58) Field of Classification Search ............ None
See application file for complete search history.

(56) References Cited

U.S. PATENT DOCUMENTS 3,325,446 A * 6/1967 Chang et al. ............ 524/89

FOREIGN PATENT DOCUMENTS

EP    455471 A2 * 11/1991
JP    02306916 A * 12/1990

OTHER PUBLICATIONS

Chodowska-Palicka, et al., "Copper (I) Oxide-Promoted Arylation of Benzothiazole with Iodoarenes", Synthesis, vol. 2, pp. 128-129 (1974).*

* cited by examiner

*Primary Examiner*—Rebecca Anderson
*Assistant Examiner*—Michael P. Barker
(74) *Attorney, Agent, or Firm*—Pillsbury Winthrop Shaw Pittman, LLP

(57) ABSTRACT

A compound of general structure I, wherein the compound is optionally in the form of an N-oxide or S-oxide

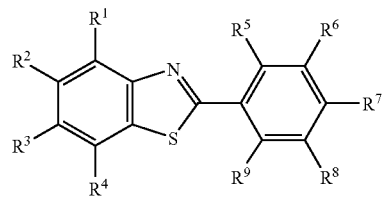

I or prodrug form and/or pharmaceutically acceptable salt thereof wherein:
each of $R^1$ to $R^9$ is independently selected from hydrogen, hydroxyl, alkoxy, halo, mesyl, $CX_3$ (X=halo), $-O(CH_2)_nNYZ-$, substituted or unsubstituted lower alkyl, substituted or unsubstituted heteroalkyl, substituted or unsubstituted aryl or heteroaryl, and substituted or unsubstituted aralkyl or heteroaralkyl;
optionally $R^6$ and $R^7$ together form a dioxymethylene ($-OCH_2O-$) unit
and wherein
n is 1 to 3 and
Y and Z are independently selected from any of the following: $C_1$-$C_6$ straight chain, branched or cyclic substituted or unsubstituted alkyl group, Y and Z can be taken together to form a cyclic alkyl or hetereoalkyl group wherein in addition to N the hetereoalkyl group comprises a heteroatom selected from N, O or S.

5 Claims, 12 Drawing Sheets

2-ARYLBENZOTHIAZOLE DERIVATIVES

Priority is claimed from U.S. Provisional Patent Appl. No. 60/605,715 filed Aug. 31, 2004.

The present invention relates to novel arylbenzothiazole compounds which find particular utility in the treatment of cancer.

Various arylbenzothiazole compounds have been found to be active in inhibiting proliferation of certain tumour cells. Compounds which have been found to be particularly active against breast cancer cell lines are aminoarylbenzothiazoles such as those described in WO 95/06469.

The compounds with which the present invention is concerned are substituted 2-arylbenzothiazole compounds, in particular those bearing oxygenated substituents on the phenyl ring and a fluoro substituent on the benzothiazole moiety, which comprise novel or new chemical entities and which are of particular interest as active chemotherapeutic agents for use in therapy, especially antitumour therapy, by virtue of an ability to inhibit proliferation of certain tumour cells.

The present invention envisages the use of substituted 2-arylbenzothiazole compounds as specified for making medicaments or pharmaceutical compositions for use in antitumour therapy for the treatment of selected cancers.

Thus, according to a first aspect of the present invention there is provided a compound of general structure I, wherein the compound is optionally in the form of an N-oxide or S-oxide

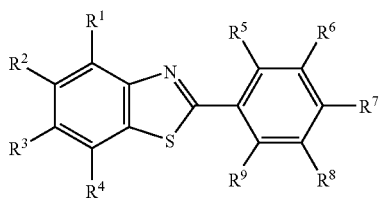

I or prodrug form and/or pharmaceutically acceptable salt thereof wherein:

$R^1$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl;

$R^2$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl;

$R^3$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl;

$R^4$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl;

$R^5$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl, $-OCO-A$- wherein A is selected from lower alkyl, substituted and unsubstituted phenyl, cycloalkyl which optionally comprises at least one heteroatom selected from N, S or O.

$R^6$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl, $-OCO-A$- wherein A is selected from lower alkyl, substituted and unsubstituted phenyl, cycloalkyl which optionally comprises at least one heteroatom selected from N, S or O.

$R^7$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl, $-OCO-A$- wherein A is selected from lower alkyl, substituted and unsubstituted phenyl, cycloalkyl which optionally comprises at least one heteroatom selected from N, S or O.

$R^8$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl, $-OCO-A$- wherein A is selected from lower alkyl, substituted and unsubstituted phenyl, cycloalkyl which optionally comprises at least one heteroatom selected from N, S or O.

$R^9$ is independently selected from hydrogen, hydroxyl, alkoxy, halo, mesyl, $CX_3$ (X=halo), $-O(CH_2)_nNYZ$-, substituted or unsubstituted lower alkyl, substituted or unsubstituted heteroalkyl, substituted or unsubstituted aryl or heteroaryl, and substituted or unsubstituted aralkyl or heteroaralkyl, $-OCO-A$- wherein A is selected from lower alkyl, substituted and unsubstituted phenyl, cycloalkyl which optionally comprises at least one heteroatom selected from N, S or O;

and optionally, $R^6$ and $R^7$ are taken together to form a methylenedioxy unit ($OCH_2O$) and wherein n is 1 to 3; and Y and Z are independently selected from any of the following: H, $C_1$-$C_8$ straight chain, branched or cyclic substituted or unsubstituted alkyl group, optionally Y and Z are taken together to form a cyclic alkyl or heteroalkyl group wherein in addition to N the heteroalkyl group comprises a heteroatom selected from N, O or S, The term "halo" is used herein to denote a halogen atom which is selected from fluorine, chlorine, bromine or iodine.

The term "lower alkyl" is used herein to denote a cyclic, branched or straight chain saturated hydrocarbon having one to six carbon atoms. Suitable examples include, but are not limited to methyl, ethyl, propyl or cyclohexyl.

The term "alkoxy" is used herein to denote a lower alkyl group, as hereinbefore defined, which is linked to a second chemical structure by way of an oxygen atom. Suitable examples include, but are not limited to methoxy, ethoxy, propoxy or methoxymethyleneoxy.

The term "substituted phenyl" is used herein to denote a phenyl group substituted with at least one functional group.

The term "cycloalkyl" is used herein to denote a cyclic saturated hydrocarbon having from five to seven carbon atoms. The said cycloalkyl may optionally comprise at least one heteroatom selected from N, S or O. Suitable examples include, but are not limited to, morpholine, furan or pyrrole.

The term "aryl" is used herein to denote a carbocyclic group or structure having at least one aromatic ring. The said ring may form part of a multiple condensed ring structure, for example phenyl, naphthalene, anthracene.

The term "aralkyl" is used herein to denote an alkyl, as hereinbefore defined, in which there is an aryl group, as hereinbefore defined, for example benzyl.

The term "heteroaryl" is used herein the denote an aryl group, as hereinbefore defined in which said group comprises at least one heteroatom, selected from, for example N, O or S, in said at least one aromatic ring. Suitable examples include, but are not limited to pyrindine, pyrrole, furan, thiophene and imidazole.

The term "heteroaralkyl" is used herein to denote an aralkyl substituents, as hereinbefore defined, in which said at least one aromatic ring comprises at least one heteroatom selected from, for example N, O or S. Suitable examples include, but are not limited to methyl pyridine and methylfuran.

The term "substituted" is used herein to denote substitution of a particular group with at least one functional group.

As referred to herein suitable functional groups include, but are not limited to, any of the following which may be used alone or in combination: hydroxyl, hydroxyalkyl, acyl, acetamide, carboxyl, cyano, carboxamide, sulfonamide, sulfone, oxide, alkoxy, nitro.

Compounds of the present invention which conform to formula I, and which are of particular interest, include compounds where the combination of substituents $R^1$ to $R^9$ are selected from the following combination:

| Cpd No | $R^1$ | $R^2$ | $R^3$ | $R^4$ | $R^5$ | $R^6$ | $R^7$ | $R^8$ | $R^9$ |
|---|---|---|---|---|---|---|---|---|---|
| 1(GW 610 NSC 721648 | H | F | H | H | H | OMe | OMe | H | H |
| 2 | F | H | H | H | H | OMe | OMe | H | H |
| 3 | H | H | F | H | H | OMe | OMe | H | H |
| 4 | H | H | H | H | H | OMe | OMe | H | H |
| 5 | H | F | H | H | H | OH | OMe | H | H |
| 6 | H | F | H | H | H | OMe | OH | H | H |
| 7 | H | F | H | H | H | —OCH$_2$O— | | H | H |
| 8 | H | H | H | H | H | —OCH$_2$O— | | H | H |
| 9 | H | F | H | H | H | OH | OH | H | H |
| 10 | H | H | H | H | H | OH | OH | H | H |
| 11 | H | F | H | H | H | OAc | OMe | H | H |
| 12 | H | F | H | H | H | OCOEt | OMe | H | H |
| 13 | H | F | H | H | H | OCO-n-Pr | OMe | H | H |
| 14 | H | F | H | H | H | OCOPh | OMe | H | H |
| 15 | H | F | H | H | H | OCO-2-Cl—Ph | OMe | H | H |
| 16 | H | F | H | H | H | OCO-2-Br—Ph | OMe | H | H |
| 17 | H | F | H | H | H | OCO-3-NO$_2$—Ph | OMe | H | H |
| 18 | H | F | H | H | H | OCO-4-NO$_2$—Ph | OMe | H | H |
| 19 | H | F | H | H | H | OCO-morph | OMe | H | H |
| 20 | H | F | H | H | H | OMe | OCO-Morph | H | H |
| 21 | H | F | H | H | H | OMe | OCO-3-NO$_2$—Ph | H | H |
| 22 | H | F | H | H | H | Me | OMe | H | H |
| 23 | H | Cl | H | H | H | OMe | OMe | H | H |
| 24 | H | Br | H | H | H | OMe | OMe | H | H |
| 25 | H | F | H | H | H | F | OMe | H | H |
| 26 | H | F | H | H | H | Cl | OMe | H | H |
| 27 | H | F | H | H | H | Br | OMe | H | H |
| 28 | H | F | H | H | H | I | OMe | H | H |
| 29 | H | F | H | H | H | H | OMe | H | H |
| 30 | Me | H | H | H | H | H | OH | H | H |
| 31 | H | F | H | H | H | H | OH | H | H |
| 32 | H | CF | H | H | H | H | OH | H | H |
| 33 | H | H | F | H | H | H | OH | H | H |
| 34 | H | H | Cl | H | H | H | OH | H | H |
| 35 | H | H | Br | H | H | H | OH | H | H |
| 36 | H | H | Et | H | H | H | OH | H | H |
| 37 | H | H | OMe | H | H | H | OH | H | H |
| 38 | H | H | OEt | H | H | H | OH | H | H |
| 39 | H | H | —SO$_2$Me | H | H | H | OH | H | H |
| 40 | H | Me | Me | H | H | H | OH | H | H |
| 41 | H | F | H | H | H | OH | H | H | H |
| 42 | H | F | H | H | H | OMe | H | OMe | H |
| 43 | H | F | H | H | H | OMe | OMe | OMe | H |
| 44 | H | F | H | H | H | OMe | OCH$_2$OCH$_3$ | H | H |
| 45 | H | F | H | H | H | OEt | OMe | H | H |
| 46 | H | F | H | H | H | OEt | OEt | H | H |
| 47 | H | F | H | H | H | OCOBu | OMe | H | H |
| 48 | H | H | H | F | H | OMe | OMe | H | H |
| 49 | H | F | H | H | H | OCO-3-NO$_2$—Ph | OMe | H | H |
| 50 | H | F | H | H | OMe | OMe | OMe | H | H |

-continued

| Cpd No | R¹ | R² | R³ | R⁴ | R⁵ | R⁶ | R⁷ | R⁸ | R⁹ |
|---|---|---|---|---|---|---|---|---|---|
| 51 | H | F | H | H | H | O(CH$_2$)$_3$Br | OMe | H | H |
| 52 | H | F | H | H | H | O(CH$_2$)$_3$.morph | OMe | H | H |
| 53 | H | F | H | H | H | OMe | OMe | H | H |
| 54 | H | H | H | H | H | OMe | OMe | H | H |
| 101 | H | H | H | H | H | Me | NH$_2$ | H | H |
| 102 | H | F | H | H | H | Me | NH$_2$ | H | H |

101 and 102 are provided by way of comparison only

Preferably, at least one of $R^1$-$R^4$ is a halogen atom and most preferably is fluorine.

Preferably, $R^6$ and $R^7$ are alkoxy groups and most preferably methoxy.

Preferably the compounds of the resent invention exist in an N-oxide or S-oxide from.

Thus, according to a second aspect of the present invention there is provided a compound of formula II, wherein the compound is optionally in the form of an N-oxide or a S-oxide.

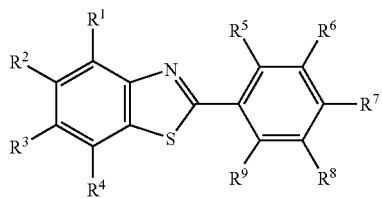

II or prodrug form and/or pharmaceutically acceptable salt thereof.

wherein anyone of $R^1$ to $R^4$ is F;

$R^6$ and $R^7$ are methoxy;

and the remaining R substituents are H.

It will be understood that where reference is made in this specification to compounds of formula I or formula II, such reference should be construed as extending also to their pharmaceutically acceptable salts and to other pharmaceutically acceptable bioprecursors (prodrug forms) where relevant. The term prodrug is used in the present specification to denote modified forms or derivatives of a pharmacologically active compound which biodegrade or are modified in vivo so as to become converted into said active compound after administration, especially intravenous administration, in the course of therapeutic treatment of a mammal. Such prodrugs are commonly chosen because of an enhanced solubility in aqueous media which helps to overcome formulation problems, and also in some cases to give a relatively slow or controlled release of the active agent. Alternatively, unmodified compounds (compound 1) may be considered for oral administration without conversion to water-soluble forms.

It should also be understood that where any of the compounds, particularly prodrug forms thereof comprising at least one chiral centre, referred to can exist in more than enantiomeric and/or diastereomeric form, all such forms, mixtures thereof, and their preparation and uses are within the scope of the present invention. It should be noted, however, that where stereochemical considerations are likely to be important there may be considerable selectivity such that different enantiomers or diastereoisomers have significantly different inhibiting activity.

The compounds of the present invention, in particular those of formula II have been shown to elicit potent and selective antitumour activity in vitro. Sensitive cell lines are clustered within colon and lung panels but also include breast and renal cell lines (see FIG. 1). Also, the GI$_{50}$ (the concentration of a particular compound required to inhibit cell growth by 50%) values have been found to be the nM range.

Although, the pattern of activity is similar to that of the antitumour fingerprint for the aminophenylbenzothiazoles of WO 95/06469, it does differ notably with respect to certain cell lines, in particular some colon and lung cell lines, which are not sensitive to the aminophenylbenzothiazole class of agents.

Advantageously, the compounds of the present invention not only exhibit a selective antitumour effect, but do so against a wider range of tumour cells than known benzothiazole derivatives.

In order to understand the difference in activity between the aminophenyl benzothiazole derivatives and the arylbenzothiazoles of the present invention the following experiments have been conducted using compound 1, i.e. 2-(3,4-dimethoxyphenyl)-5-fluorobenzothiazole (GW 610):

Induction of cyp 1a1 Transcription:

Compound 1 was able to induce cyp 1a1 gene transcription in MCF-7, T-47D, TK-10, NC1 and 1460 cells. These cell lines are known to be sensitive to compound 1 and 2-(4-amino-3-methylphenyl)-5-fluorobenzothiazole (102, 5F 203; NSC 703786; WO 95/06469) In cell lines which are sensitive to compound 1 only, cyp 1a1 gene transcription was not induced. Therefore, induction of cyp 1a1 does not appear to be requisite for sensitivity to compound 1.

These findings have been verified following examination of induction of cyp 1a1 protein expression by Western Blot. The following cell lines were used to represent sensitive models: MCF-7, MDA 468 (breast carcinoma), KM12 and HCC 2998 (colon carcinoma) lines. Induction of cyp 1a1 protein was observed in lysates of MCF-7 and MDA 468 breast cells treated with compound 1 (100 nM to 10 μM). However, cyp 1a1 protein was not induced in either colon cell line Moreover, inactive analogues (GI$_{50}$ values>100 μM) e.g. 2-(3,4-dioxymethylene) benzothiazole (NSC 725530) were able to induce cyp 1a1 protein expression in the two breast cell lines.

Inhibition of cyp 1a1 Activity Using Resveratrol:

Resveratrol is able to block the activity of agents of the 2-(4 aminophenyl) benzothiazole class (e.g. 2-(4-amino-3-methylphenyl)benzothiazole; 101; DF 203; NSC 674495; FIG. 3a) and compound 102 (NSC 703786; Hose et al, Molecular Cancer Therapeutics 2003, 2, 1265-1272) in aminophenyl benzothiazole sensitive cells with inducible cyp 1a1. However, resveratrol has no effect on the growth inhibitory activity of compound 1 (FIG. 3b), further refuting a role for cyp 1a1 in compound 1 antitumour activity.

Inhibition of cyp 1a1 Activity:

Compound 1 inhibits cyp 1a1 (EROD) activity in a dose dependent manner ($IC_{50}$=8 µM; FIG. 4).

Induction of cvp 1b1 Transcription:

As with cyp 1a1 induction, cyp 1b1 gene transcription can be induced by compound 1. Again, this characteristic appears unrelated to its mode of action as there are certain compound 1-sensitive colon and lung carcinoma cells which demonstrate no induction of cyp-1b1 transcription (see FIG. 5).

DNA Adduct Formation:

Two distinct major adducts and one minor adduct are generated in the DNA of MCF-7, MDA 468, KM12 and HCC 2998 cells following treatment with compound 1 (1 µM; FIG. 6).

Other Analogues 2-(3,4-Dimethoxyphenyl-4-fluorobenzothiazole (4F610; compound 2) exhibits substantial potent and selective antitumour activity. Again, sensitive cell lines are heavily clustered within the lung and colon panels and nM $Gl_{50}$ so values are observed. Compound 3 (2-(3,4-dimethoxyphenyl)-6-fluorobenzothiazole; 6F 610) also demonstrates antitumour activity in vitro.

Generation of DNA adducts: One major adduct species is formed in the DNA of MCF-7, MDA 468, KM12 and HCC 2998 cells following treatment with compound 2. The number of adducts generated per $10^8$ nucleotides correlates with cell line sensitivity to this analogue: MCF-7>MDA 468>KM12 HCC 2998 ($GI_{50}$ values 2.9 nM, 3.4 nM, 78.4 nM, 4.9 µM, respectively).

Biological Results and Discussion

The following discussion relates to the biological activity of the various analogues described herein:

A range of compounds were evaluated in MTT assays following 3 day exposure against a panel of two human breast cancer cell lines MCF-7 (ER+) and MDA 468 (ER−), and two colon cancer cell lines KM12 and HCC 2998. In general the breast cell lines were more sensitive to the agents and the MDA 468 line the most sensitive of the four (Table 2). The benchmark active compound was 5-fluoro-2-(3,4-dimethoxyphenyl)benzothiazole (1) with $GI_{50}$ values<0.1 nM against the two breast cell lines. Compounds with no substituent in the benzothiazole moiety (4,8) retained sub-micromolar activity against MDA 468 but were inactive against the MCF-7, KM12 and HCC 2998 lines ($GI_{50}$ values>10 µM). Introduction of a 5-fluoro group generally enhanced potency: compounds with a single methoxy group such as 5-fluoro-2-(4-methoxyphenyl)benzothiazole (29), and other analogues with a 4'-methoxyphenyl group (22,25, 26,27,28) bearing a methyl or halogen replacement for methoxy in the 3'-position were comparable in activity; 5-fluoro-2-(4-methoxy-3-methyl-phenyl)benzothiazole (22) was the most potent with $GI_{50}$ values 0.048 and 0.058, µM against MCF-7 and MDA 468, respectively. The most interesting series of compounds were those combining a 5-fluoro group with two oxygenated substituents in the 3',4'-positions where minor, seemingly conservative, structural changes were associated with a dramatic variations in activity (when compared to 1). Thus replacement of either (or both) of the methoxy groups by hydroxyl (9,5,6), methylenedioxy (7), methoxymethyleneoxy (MOM; 44), or ethoxy substituents (45,46) had a dyschemotherapeutic effect. Similarly, the analogue with a 3',5'-disposition of methoxy groups (42) had only low micromolar inhibitory potency whereas the 3',4',5'-trimethoxy congener (43) retained nanomolar inhibitory potency against the MCF-7 cell and MDA 468 cell lines. Of this group of compounds the diethoxy analogue (46) was the most potent against the MCF-7 cell ($GI_{50}$ value 0.7 nM). Surprisingly, replacement of the 5-fluoro group of 1 with a 5-chloro-(23) or 5-bromo-substituent (24) essentially abolished inhibitory potency, whereas the 6-(3) and 4-fluoro regioisomer (2) retained nanomolar growth inhibitory potency against one or more of the cell lines. In summary, this in vitro screen led to the identification of the fluorinated 2-(3,4-dimethoxyphenyl)benzothiazole structure as a novel antitumor pharmacophore with the 5-fluoro analogue (1) astride a pinnacle of activity.

TABLE 2

Activity of Benzothiazoles Against Human Breast and Colon Cancer Cell Lines[a]

| compd | $GI_{50}$ values (µM)[b] in cell lines[c] | | | |
|---|---|---|---|---|
| | MCF-7 | MDA 468 | KM 12 | HCC 2998 |
| 101[e] | <0.0001 | <0.0001 | >100 | >100 |
| 102[f] | <0.0001 | <0.0001 | >100 | >100 |
| 10 | | | | |
| 8 | 57.8 | 0.80 | 98.6 | 68.3 |
| 4 | 52.7 | 0.53 | 74.2 | 42.5 |
| 29 | 0.49 | 0.33 | 24.6 | 12.4 |
| 22 | 0.048 | 0.058 | 18.6 | 0.54 |
| 25 | 0.87 | 0.64 | 20.6 | 13.7 |
| 26 | 0.76 | 0.48 | 7.05 | 2.5 |
| 27 | 0.85 | 0.42 | 6.7 | 3.45 |
| 28 | 0.82 | 0.36 | 6.9 | 0.94 |
| 9 | | | | |
| 7 | 20.7 | 0.57 | 25.1 | 22.3 |
| 5 | 0.5 | 0.05 | 18.4 | 7.6 |
| 6 | | | | |
| 1 | <0.0001 | <0.0001 | 0.29 | 0.00025 |
| 42 | 1.23 | 0.31 | 7.55 | 5.21 |
| 43 | 0.0019 | 0.0021 | 12.95 | 21.1 |
| 44 | 0.065 | 0.048 | 19.25 | 53.5 |
| 45 | 0.080 | 0.092 | 5.42 | 3.32 |
| 46 | 0.0007 | 0.055 | 38.5 | |
| 23 | 27.92 | 1.00 | 12.4 | 4.88 |
| 3 | 0.062 | 0.005 | 24.07 | 6.21 |
| 2 | 0.005 | 0.005 | 0.85 | 1.06 |
| 48 | | | | |
| 24 | 13.6 | 0.77 | 65.15 | 20.0 |
| 19 | 0.085 nM | 0.64 nM | 7.14 | 7.53 |
| 53 | 0.92 | 0.76 | >100 | 40.3 |
| 50 | 156.8 nM | 336.4 nM | 2905.3 nM | 203.1 nM |

[a]Determined by MTT assay, see Biological Experimental for details.
[b]Compounds tested in triplicate.
[c]Cancer cell line origin: MCF-7 (breast), MDA 468 (breast), KM 12 (colon), HCC 2998 (colon).
[e]2(4-amino-3-ethylphenyl)benzothiazole.
[f]5-fluoro-2(4-amino-3-methylphenyl)benzothiazole. (e and f are given by way of comparison)

Results from the more extensive NCI in vitro 60 human cancer cell panel[15] corroborated the results (above). The mean $GI_{50}$ values across the range of compounds (above), including the two series of esters (11-21) are an unremarkable 10-100 µM (data not shown); however, these values disguise significant cell selectivity. For example, compound (1) has exquisite activity in the colon and NSCL sub-panels (FIG. 1) with $GI_{50}$ values<10 nM against some cell lines: the requirement for a fluoro group was confirmed in the attenuated pattern of activity of 2-(3,4-dimethoxyphenyl)benzothiazole (4) (FIG. 8). This result contrasts from our earlier experience in the related 2-(4-aminophenyl)benzothiazole series[4,5,12-14] where the characteristic cell line selectivity of 2-(4-amino-3-methylphenyl)-5fluorobenzothiazole (102) is also displayed by its non-fluorinated counterpart (101). The mean $GI_{50}$ graphs of the 4-fluoro- (2) and 6-fluoro-2-(3,4-dimethoxyphenyl)benzothiazoles (3) showed potent (but attenuated compared to 1), activity in the colon and NSCL sub-panels. Full NCI mean $GI_{50}$ graphs for compounds (1,2,3,4,101,102) are included herein as FIGS. 1 and 8 to 12.

The present invention also relates to the therapeutic utility of the arylbenzothiazole compounds described herein.

Thus, according to a further aspect of the present invention there is provided an arylbenzothiazole compound as hereinbefore defined for use in therapy. More specifically, the present invention also provides an arylbenzothiazole compound as hereinbefore defined for use as an active pharmaceutical substance for the treatment of cancer.

As referred to herein "cancer" or "tumour" includes, but is not limited to, cancer of the lung, colon, pancreas, stomach, ovary, cervix, breast, prostate, bone, brain or skin.

In a further aspect of the present invention there is provided the use of at least one arylbenzothiazole compound as herein before defined in the manufacture of a medicament.

According to a further aspect of the present invention there is provided the use of at least one arylbenzothiazole compound as hereinbefore defined in the manufacture of a medicament for the treatment of cancer.

The compounds of the present invention, and particular those of formula II, have been shown to inhibit the proliferation of certain tumour cells, especially lung and colon cells.

According to a still further aspect of the present invention there is provided the use of at least one arylbenzothiazole compound as hereinbefore defined in the manufacture of a medicament for the treatment of lung and/or colon and/or breast cancer.

Accordingly, the compounds of the present invention are of particular interest for the treatment of a range of selected cancer tumours, and the invention further provides a method for the treatment of a patient suffering from cancer.

Thus, according to a further aspect of the present invention there is provided a method for the treatment of a mammal suffering from cancer, comprising the steps of: administering to said mammal a therapeutically effective, non-toxic amount of an aryl benzothiazole compound as hereinbefore defined.

The arylbenzothiazole may be administered orally, parenterally (including subcutaneously, intramuscularly and intravenously or topically.

The administration will generally be carried out respectively at intervals, for example once or several times a day.

The amount of the arylbenzothiazole compound as hereinbefore defined, which is required in order to be effective as an antitumour agent for treating mammals will of course vary and is ultimately at the discretion of the medical or veterinary practitioner treating the mammal in each particular case.

The factors to be considered by such a practitioner e.g. a physician, include the route of administration and pharmaceutical formulation; the mammal's body weight, surface area, age and general condition; and the physical and chemical form of the compound to be administered. However, a suitable effective antitumour dose may be in the range of about 1.0 to about 75 mg/kg bodyweight, preferably in the range of about 5 to 40 mg/kg with most suitable doses being for example in the range of 10 to 30 mg.kg. In daily treatment for example, the total daily dose may be given as a single dose, multiple doses, e.g. two to six times per day, or by intravenous infusion for any selected duration. For example, in the case of a 75 kg mammal, the dose range could be about 75 to 500 mg per day and it is expected that a typical dose would commonly be about 100 mg per day. If discrete multiple doses are indicated, treatment might typically be 50 mg of the compound of formula given 4 times per day in the form of a tablet capsule, liquid (e.g. syrup) or injection.

While it may be possible for the compounds of formula I and formula II to be administered alone as the raw chemical, it is preferable to present the compound in a pharmaceutical composition. Thus, the invention also provides pharmaceutical compositions comprising a therapeutically effective amount of an arylbenzothiazole compound as hereinbefore defined. Such pharmaceutical compositions for medical use will be formulated in accordance with any of the methods well known in the art of pharmacy for administration in any convenient manner. The arylbenzothiazole compounds will usually be admixed with at least one other ingredient providing a compatible pharmaceutically acceptable additive carrier, diluent or excipient, and may be presented in unit dosage form.

The carrier(s) must be pharmaceutically acceptable in the sense of being compatible with the other ingredients of the formulation and not deleterious to the recipient thereof.

The possible formulations include those suitable for oral, rectal, topical and parenteral (including subcutaneous intramuscular and intravenous) administration or for administration to the lung or other absorptive site such as the nasal passages.

All methods of formulation in making up such pharmaceutical compositions will generally include the step of bringing the compound of formula I or formula II into association with a carrier which constitutes one or more accessory ingredients. Usually, the formulations are prepared by uniformly and intimately bringing the compound of formula I or formula II into association with a liquid carrier or with a finely divided solid carrier or with both and then, if necessary, shaping the product into desired formulations.

Formulations of the present invention suitable for oral administration may be presented as discrete units such as capsules, cachets, tables or lozenges, each containing a predetermined amount of the compound of formula I or formula II; as a powder or granules; or a suspension in an aqueous liquid or non-aqueous liquid such as a syrup, an elixir, an emulsion or a draught. The compound of formula I may also be presented as bolus, electuary or paste.

A tablet may be made by compression or moulding, optionally with one or more accessory ingredients. Compressed tables may be prepared by compressing, in a suitable machine, the compound of formula I or formula II in a free-flowing form such as a powder or granules, optionally mixed with a binder, lubricant, inert diluent, surface active or dispersing agent. Moulded tables may be may be moulding, in a suitable machine, a mixture of the powdered compound of formula I or formula II with any suitable carrier.

A syrup may be made by adding the compound of formula I or formula II to a concentrated, aqueous solution of a sugar, for example sucrose, to which may be added any desired accessory ingredients. Such accessory ingredient(s) may include flavourings, an agent to retard crystallisation of the sugar or an agent to increase the solubility of any other ingredient, such as a polyhydric alcohol, for example glycerol or sorbitol.

Formulations for rectal administration may be presented as a suppository with a usual carrier such as cocoa buffer.

Formulations suitable for parental administration convenient comprise a sterile aqueous preparation of the compound of formula I or formula II, which is preferably isotonic with the blood of the recipient.

In addition to the aforementioned ingredients, formulations of this invention, for example ointments, creams and such like, may include one or more accessory ingredients, for example a diluent, buffer, flavouring agent, binder, surface active agent, thickener, lubricant and/or a preservative (including an antioxidant) or other pharmaceutically inert excipient.

The compounds of the present invention may also be made up for administration in liposomal formulations, which can be prepared by methods well known in the art.

Therefore, the invention also includes the use of the arylbenzothiazole compounds hereinbefore defined for the manufacture of medicaments or pharmaceutical compositions for treating cancer, wherein the arylbenzothiazole itself provides an effective antitumour agent.

The present invention also relates to the use of the compounds of the present invention in Positron Emission Tomography (PET) imaging. Compounds of the present invention bearing a fluoro substituent can be prepared using an $^{18}F$ isotope so as to provide radiolabelled compounds as hereinbefore described bearing an $^{18}F$ radiolabel. Following administration to a patient the radiolabelled compound can be traced through the body using PET imaging. Methods for incorporating an $^{18}F$ isotope into a compound are well known to those skilled in the art.

Thus according to a still further aspect of the present invention there is provided a compound of claim 1 or claim 2, wherein at least one of $R^1$ to $R^9$ is an $^{18}F$ isotope.

BRIEF DESCRIPTION OF THE DRAWINGS

The present invention will now be described further by way of example only and with reference to the following drawings.

FIG. 1 shows lung and colon cancer cells to be particularly sensitive to compound 1. The results shown on FIG. 1 were generated by treating the cells with an active agent for 48 hours, in this case compound 1, before determination of viability by sulforhodamine B assay.

FIG. 2 indicates that induction of cyp lal is not a prerequisite for sensitivity to compound 1. The results shown in FIG. 2 were generated by treating the cells with 1 µM of an active agent for 24 hours before determination of changes in cyp lal gene expression.

FIGS. 3a and 3b shows that resveratrol has no effect on the growth inhibitory activity of compound 1, further refuting a role for cyp lal in the antitumour activity of compound 1. The results shown in FIGS. 3a and 3b were generated using MCF-7 (FIG. 3a) and HCC 2998 (FIG. 3b) cells. The said cells were treated with DF 203 or compound 1, alone or in combination with resveratrol (51 µM) an inhibitor of cyp lal activity. It can be seen that in MCF-7 cells (cyp lal-inducible) the activity of DF 203 was abolished. However, compound 1 still potently inhibited the growth of these cells.

In HCC 2998 cells, possessing neither constitutive nor inducible cyp lal, resveratrol failed to compromise the growth inhibitory properties of both agents.

Figure 1:
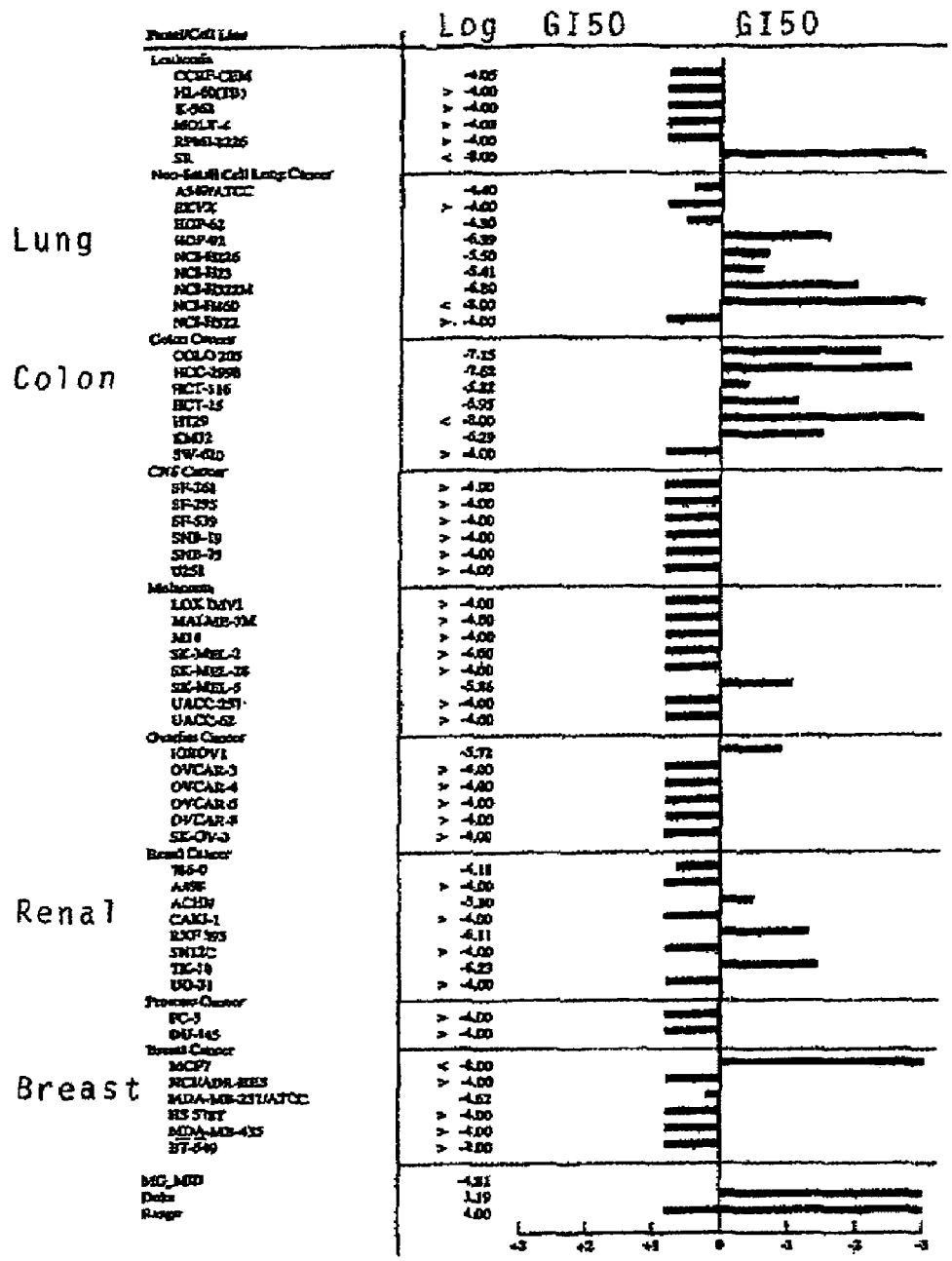
FIG. 1 is a bar chart showing the sensitivity of particular cancer cell panels to compound 1 (NSC 721648 2-(3,4-dimethoxyphenyl)-5-fluorobenzothiazole; GW 610)
Figure 2:
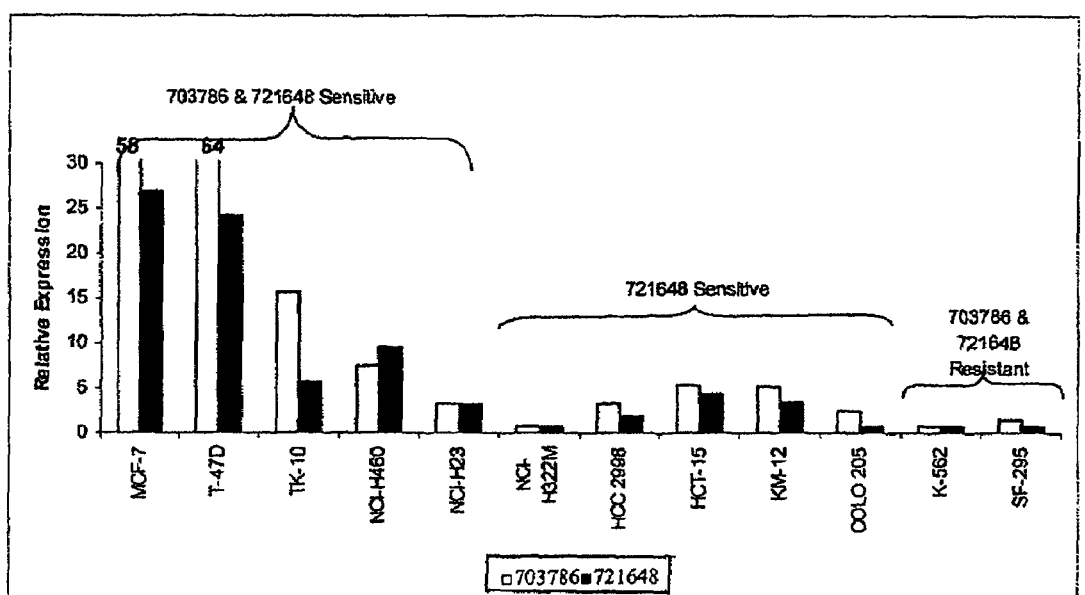
FIG. 2 is a bar chart showing the induction of cyp Ia] mRNA by 2-(4-amino-3-methylphenyl)-5-fluorobenzothiazole (102; 5F203; NSC 703786) and compound 1 (2-(3,4-dimethoxyphenyl)-5-fluorobenzothiazole; GW 610)
Figure 3A:
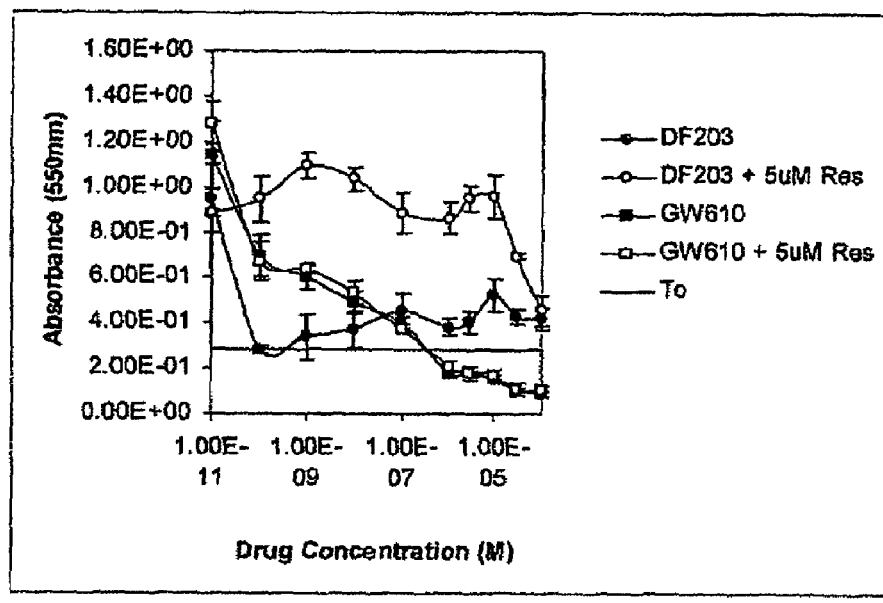
FIGS. 3a & 3b are line graphs showing the results of resveratrol incubations of MCF-7 and HCC 2998 cell lines with 2-(4-amino-3-methylphenyl)-5 fluorobenzothiazole (compound 101; DF 203; NSC 674495) and 2-(3,4-dimethoxyphenyl) 5-fluorobenzothiazole (compound 1; GW 610; NSC 721648)
Figure 3B:
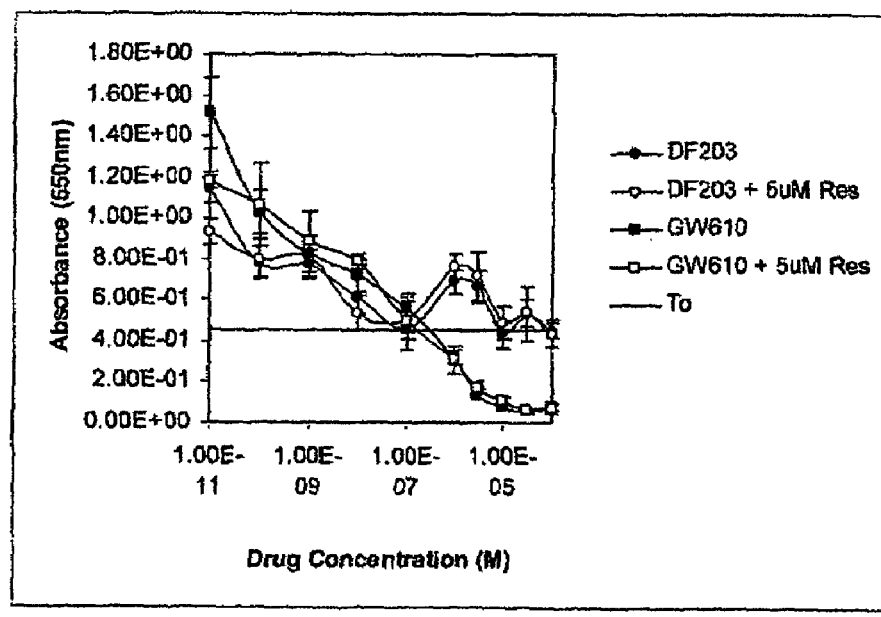
Figure 4:
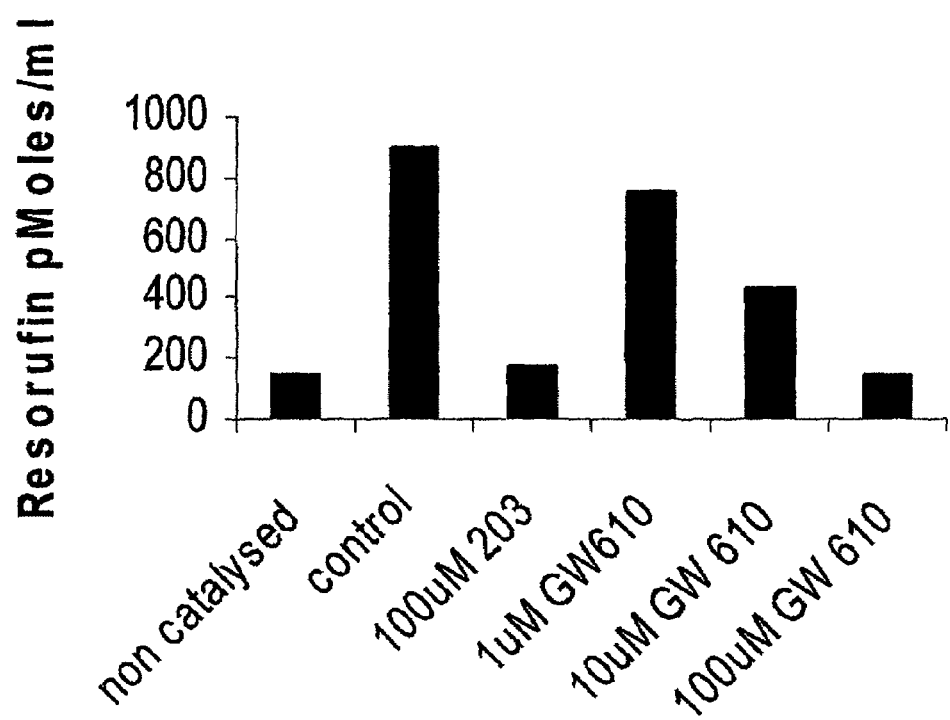
FIG. 4 is a bar chart showing the inhibitory effect of GW 610 (compound 1; NSC 721648) on cyp Ia] activity.

FIG. 4 shows that compound 1 inhibits cyp lal (EROD) activity in a dose dependent manner. The results shown in FIG. 4 were generated by measuring the de-ethylation of ethoxyresorufin by cyp lal microsomes in the absence and the presence of increasing concentrations of compound 1. DF 203 was used as a positive control.

Figure 5:
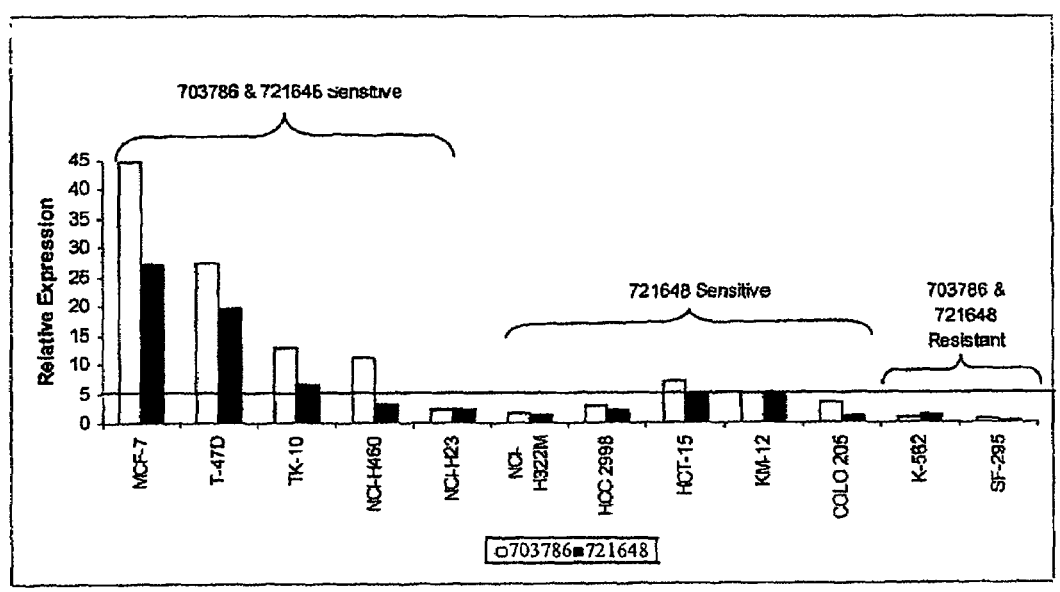
FIG. 5 is a bar chart showing the induction of cyp ib] mRNA by 2-(4-amino-3-methylphenyl)-5-fluorobenzothiazole (compound 54; 5F203; NSC 703786) and 2-(3,4-dimethoxyphenyl)-5-fluorobenzothiazole (compound 1; GW 610; NSC 721648)

FIG. 5 indicates that the mode of action of compound 1 is unrelated to cyp lal gene transcription as colon and lung cells which are sensitive to compound 1 demonstrate no induction of cyp lal gene transcription.

Figure 6:
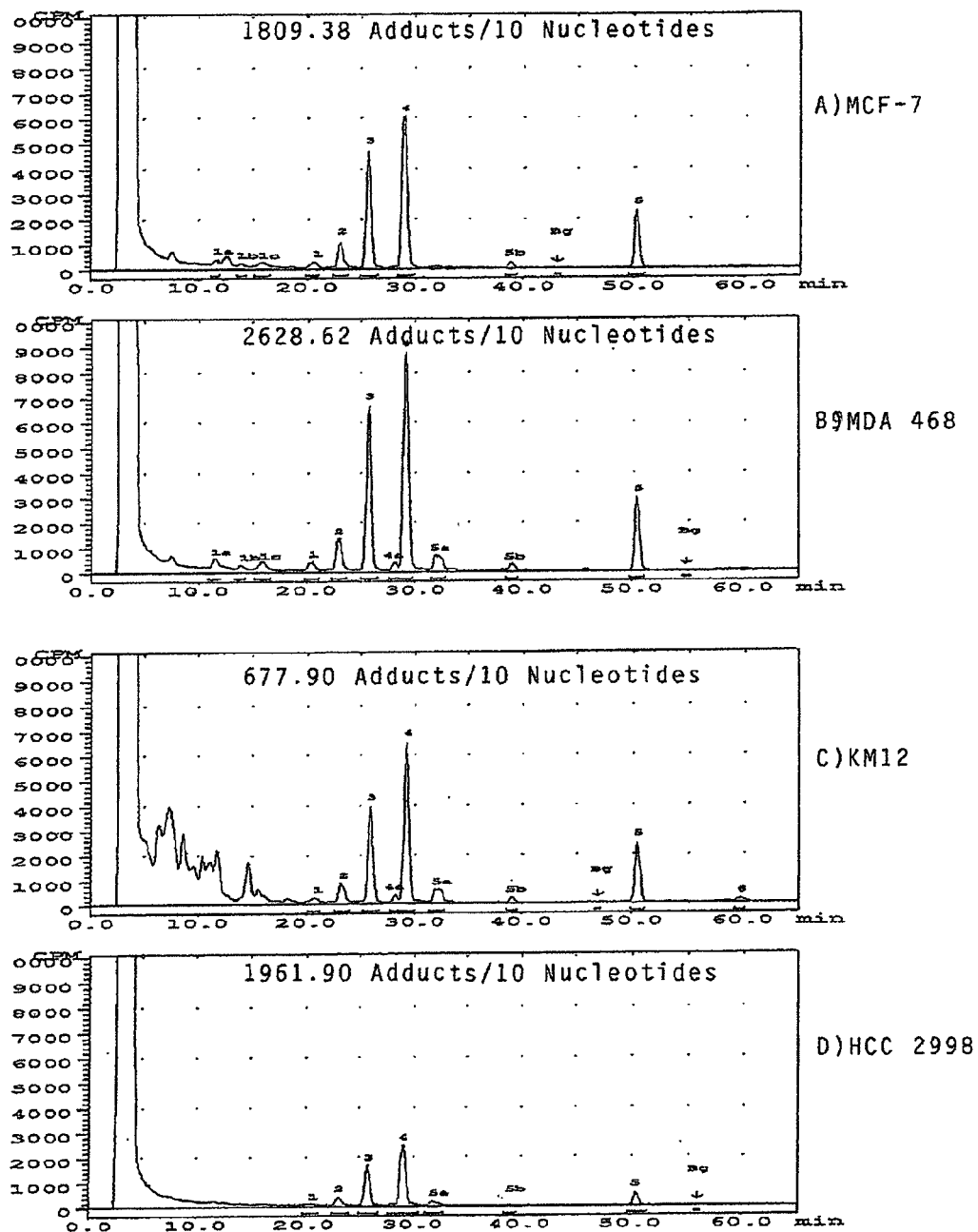
FIG. 6 shows DNA adduct formation in various cell lines following treatment with 2-(3,4-dimethoxyphenyl)-5-fluorobenzothiazole (GW 610; NSC 721648; compound 1)

FIG. 6 shows that two distinct major adducts and one minor adduct are formed in the DNA of MCF-7, MDA 468, KM 12 and HCC 2998 cells following treatment with 10 µM of compound 1 for 24 hours.

Figure 7:
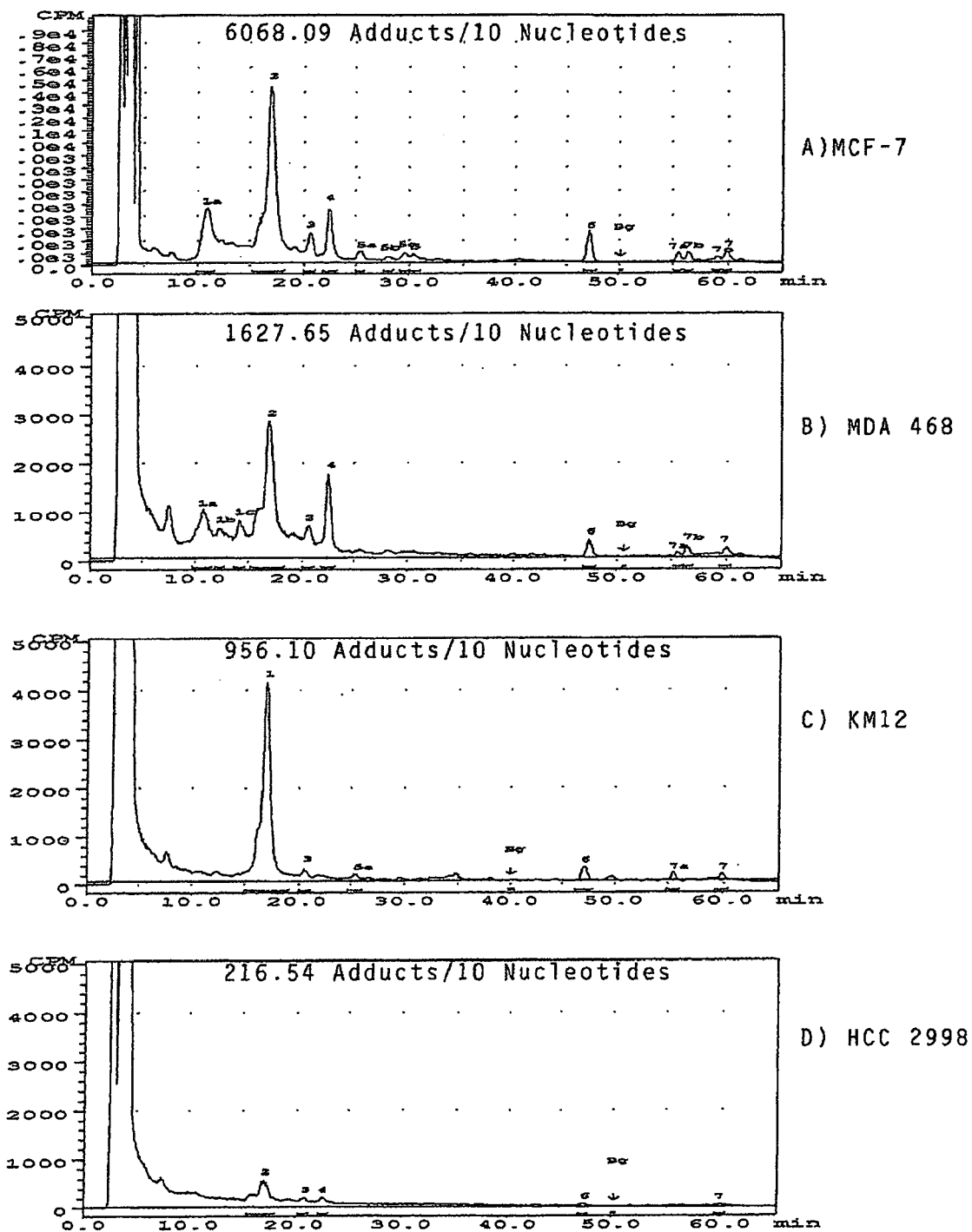
FIG. 7 shows DNA adduct formation in various cell lines following treatment with 2-(3,4-dimethoxyphenyl)-4-fluorobenzothiazole (compound 2);.

FIG. 7 shows the adducts formed in DNA of MCF-7, MDA 468, KM 12 and HCC 2998 cells following treatment of cells with 10 µM of compound 2 for 24 hours.

Figure 8:
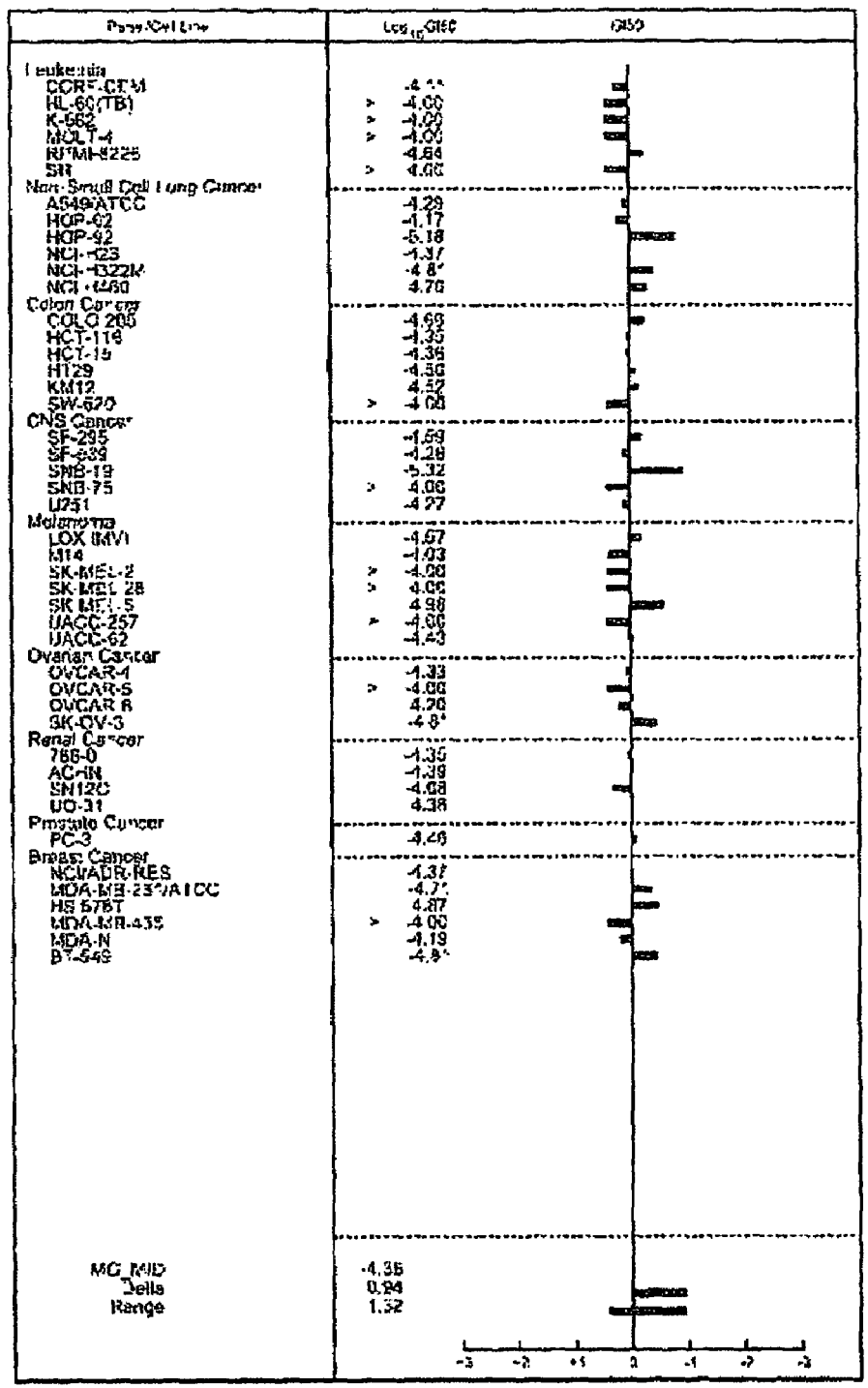
FIG. 8 is a bar chart showing the sensitivity of particular cell panels to compound 4.

FIG. 8 shows no cancer cells to be particularly sensitive to compound 4.

Figure 9:
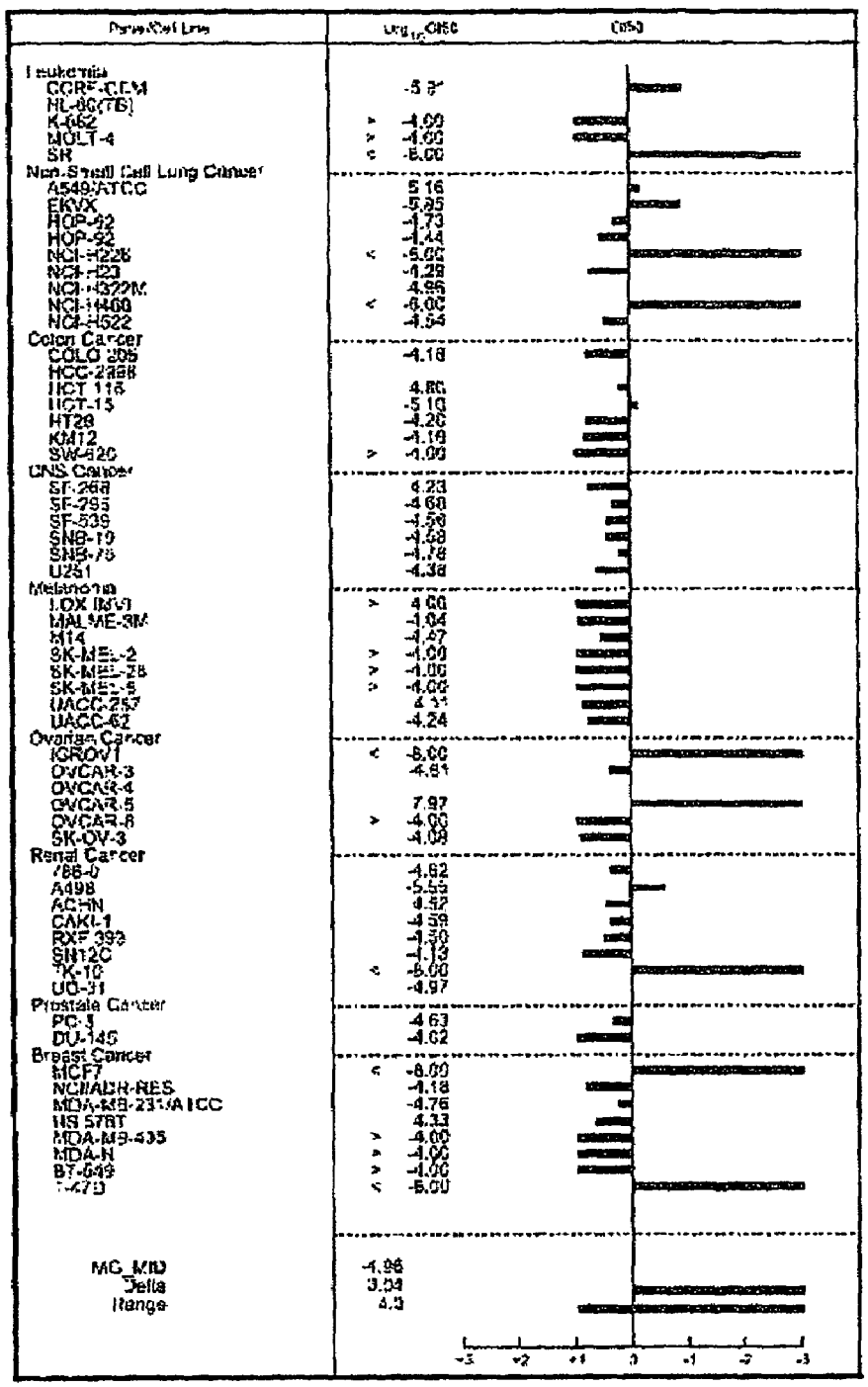
FIG. 9 is a bar chart showing the sensitivity of particular cell panels to compound 102.

FIG. 9 shows cancer cells of non-small cell lung, ovarian, renal and breast cancel cells to be particularly sensitive to compound 102.

Figure 10:
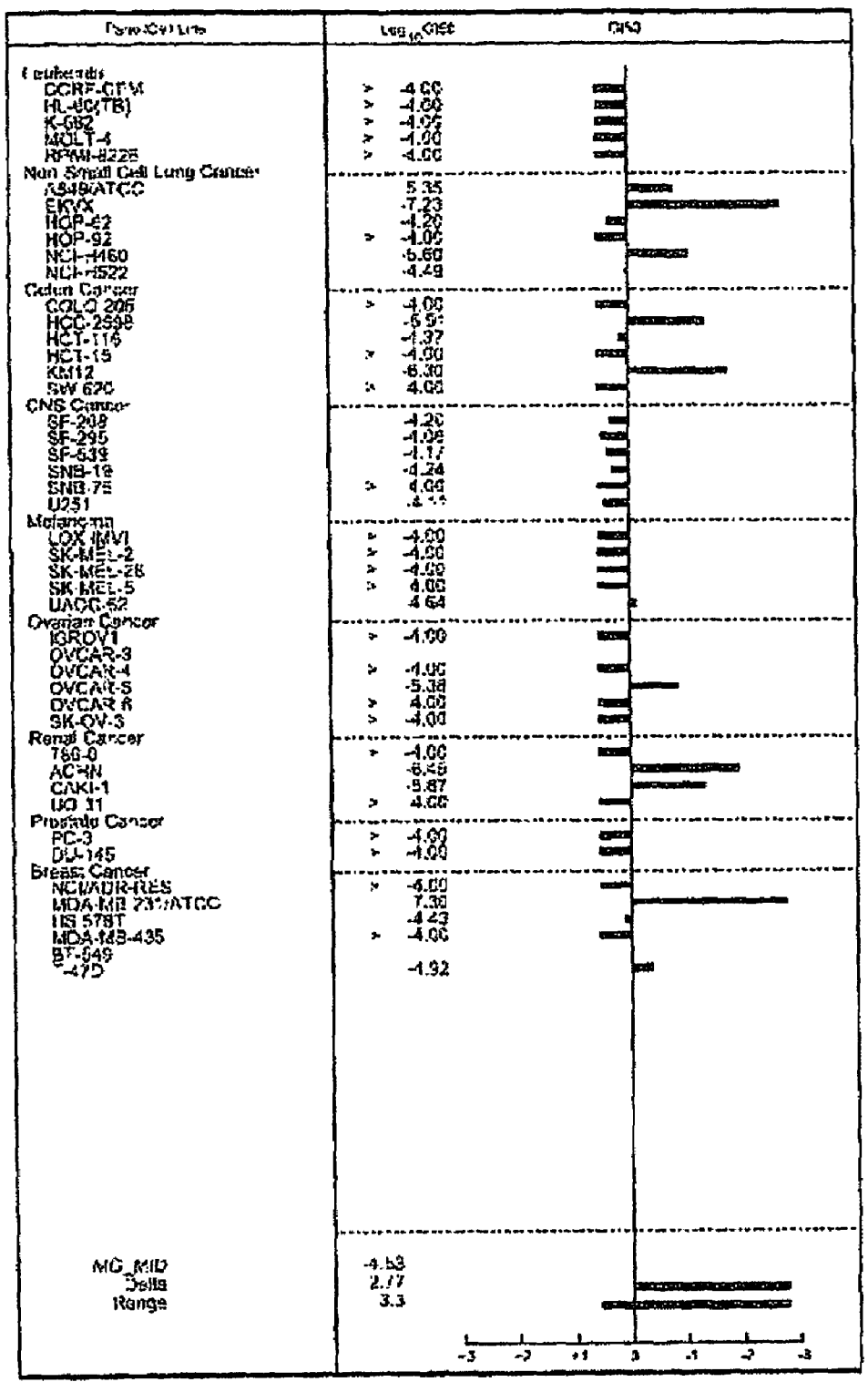
FIG. 10 is a bar chart showing the sensitivity of particular cell panels to compound 2.

FIG. 10 shows that compound 2 has a reduced activity against cancer cells when compared to compound 1.

Figure 11:
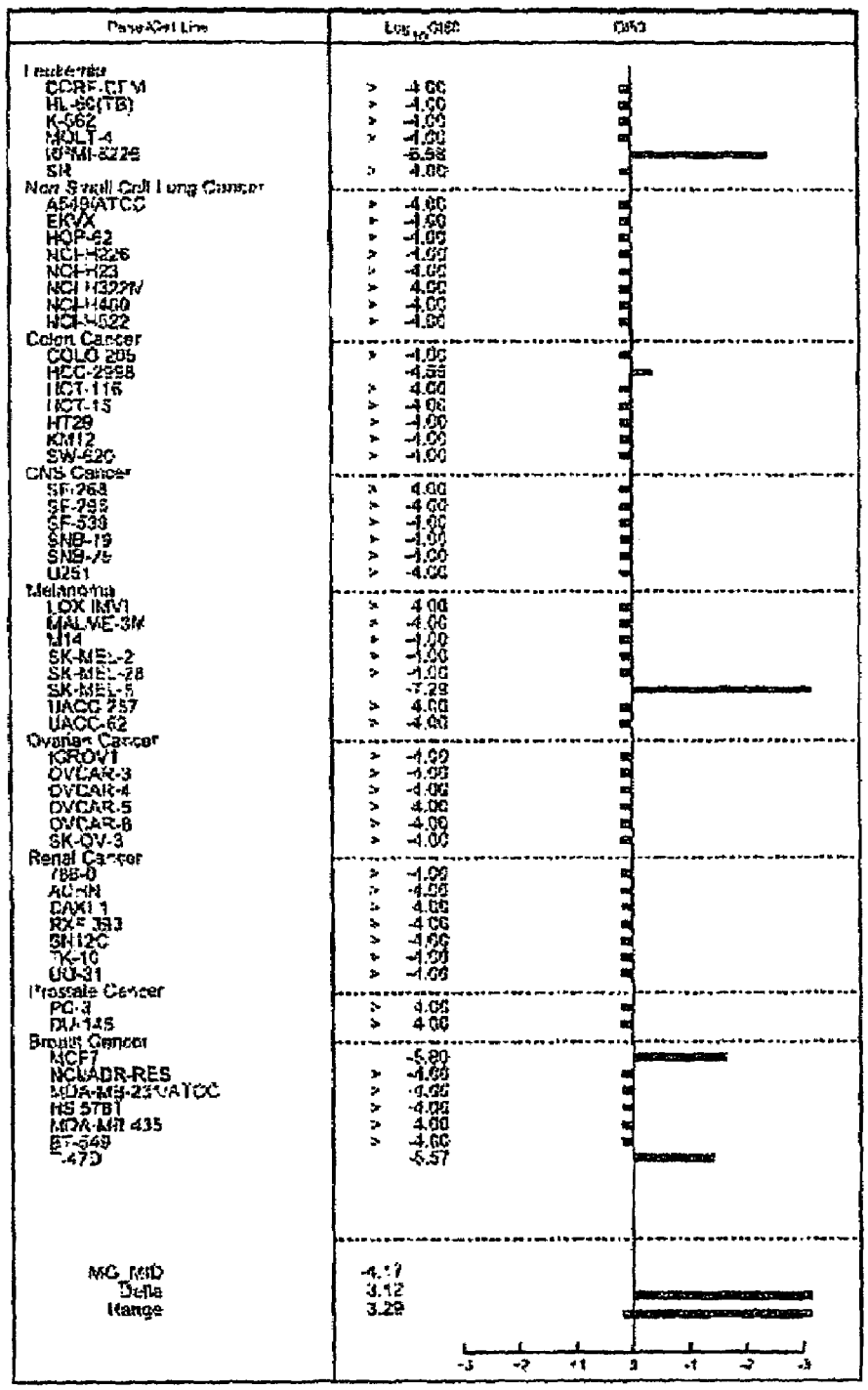
FIG. 11 is a bar chart showing the sensitivity of particular cell panels to compound 3.

FIG. 11 shows that compound 3 has a reduced activity against cancer cells when compared to compound 1

Figure 12:
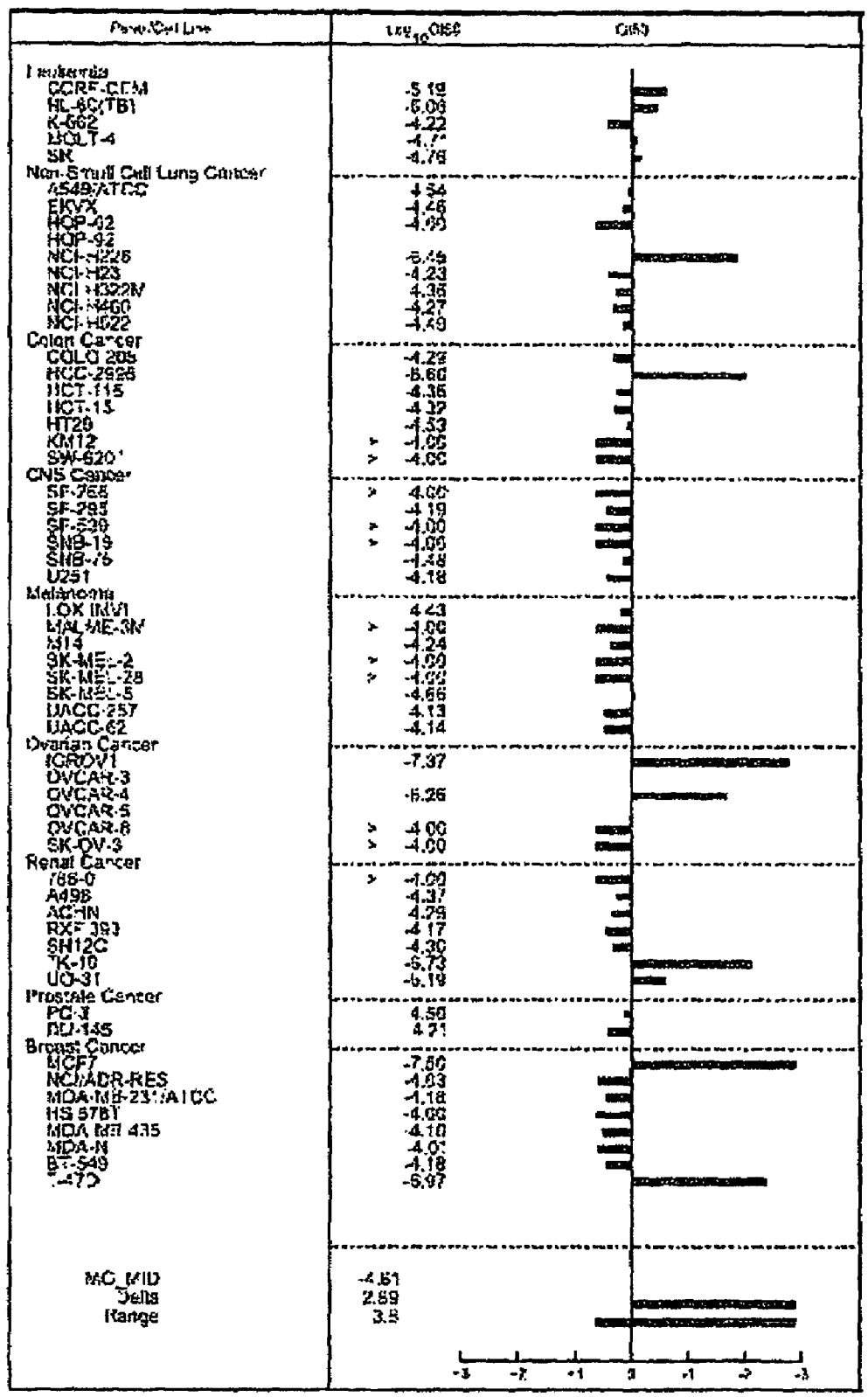
FIG. 12 is a bar chart showing the sensitivity of particular cell panels to compound 101.

FIG. 12 shows that ovarian and breast cancer cells are particularly sensitive to compound 101.

The assays/methods used to generate the results referred to herein are well known to those skilled in the art and therefore it has not been necessary to describe them in detail.

The present invention will now be described still further by way of example only. The following examples and description of stages in synthetic routes of preparation of various compounds of interest serve further to illustrate the present invention.

Synthetic Methods for the Preparation of Benzothiazoles

Chemistry. Melting points were measured on a Galenkamp apparatus and are uncorrected. IR spectra (as KBr disks) were recorded on a Perkin-Elmer Series 1 FT-IR spectrometer. Mass spectra were recorded on either a Micromass Platform spectrometer, an AEI MS-902 (nominal mass), or a VG Micromass 7070E or a Finigan MAT900XLT spectrometer (accurate mass). NMR spectra were recorded on either a Bruker AVANCE 400 MHz or Bruker ARX 250 instrument; coupling constants are in Hz. Merck silica gel 60 (40-60 μM) was used for column chromatography. All commercially available starting materials were used without further purification.

General Method A: For the Synthesis of 2-arylbenzothiazoles Unsubstituted in the Benzothiazole Ring ($R^1$=H)

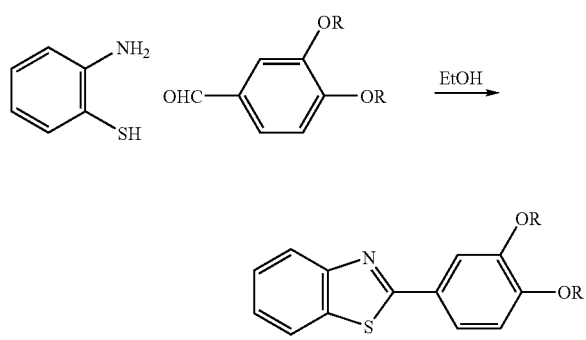

A mixture of 2-aminothiophenol (100 mmol) and 3,4-disubstituted benzaldehyde (100 mmol) in ethanol (150 mL) was heated under reflux for two hours. After cooling to room temperature, the solution was concentrated in vacuo. The residue was partitioned between water and ethyl acetate (500 mL), and the aqueous layer extracted using further ethyl acetate (2×500 mL). The combined organic layers were dried ($MgSO_4$), filtered and concentrated to give the crude product, which was recrystallised from ethanol.

The following compounds were prepared by general method A:

2-(3,4-Dimethoxyphenyl)benzothiazole (4)

From 3,4-dimethoxybenzaldehyde (50% yield), mp 141-143° C.; $^1$H NMR ($CDCl_3$) 67 8.05 (1H, d, J=7.5 Hz, H-7), 7.88 (1H, d, J=7.5 Hz, H-4), 7.72 (1H, d, J=2.3 Hz, H-2'), 7.61 (1H, dd, J=2.3, 8.0 Hz, H-6'), 7.48 (1H, dt, J=2.5, 7.5 Hz, ArH), 7.38 (1H, dt, J=2.7, 7.5, ArH), 6.96 (1H, d, J=8.0 Hz, H-5'), 4.03 (3H, s, OMe), 3.96 (3H, s, OMe); Anal. ($C_{15}H_{13}NO_2S$) C, H, N. C: found 66.35%, calc. 66.40%; H: found 4.74%, calc. 4.83%; N: found 4.94%, calc. 5.16%.

2-(3,4-Methylenedioxy)benzothiazole (8)

From 3,4-methylene-dioxybenzaldehyde (37% yield), mp 133-135° C.; $^1$H NMR ($CDCl_3$) δ 8.02 (1H, d, J=8.0 Hz, H-7), 7.88 (1H, d, J=8.0 Hz, H-4), 7.61 (2H, m, H-2', H-6'), 7.48 (1H, dt, J=1.0, 8.7 Hz, ArH), 7.37 (1H, dt, J=0.8, 8.7 Hz, ArH), 6.91 (1H, d, J=8.0 Hz, H-5'), 6.06 (2H, s, $OCH_2O$). Anal. ($C_{14}H_9NO_2S$) C, H, N. C: found 66.21%, calc. 65.87%; H: found 3.46%, calc. 3.55%; N: found 5.37%, calc. 5.49%.

General Method B: For the Synthesis of 2-arylbenzothiazoles Substituted in the Benzothiazole Ring

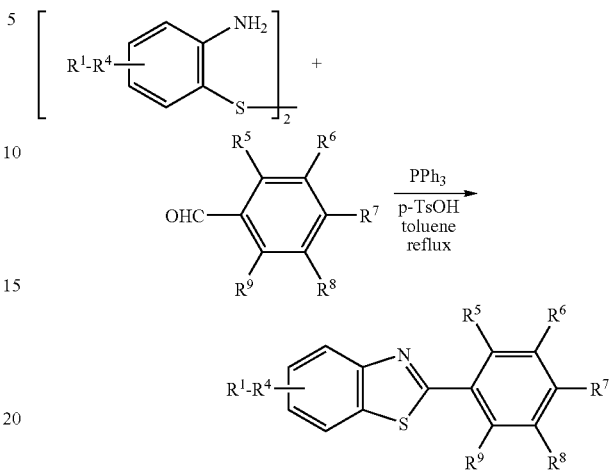

Disubstituted benzaldehyde (3.5 mmol), p-toluenesulphonic acid (0.35 mmol) and triphenylphosphine (1.75 mmol) were added to a solution of disulfide (1.75 mmol) in toluene (20 mL). The reaction mixture was heated at reflux for 24 hrs then allowed to cool and concentrated in vacuo. The crude product was purified by column chromatography (2% $MeOH/CH_2Cl_2$) to give the required substituted 2-phenylbenzothiazole in good yield.

5-Fluoro-2-(3,4-dimethoxyphenyl)benzothiazole (1).

From bis(2-amino-4-fluorophenyl)disulfide and 3,4-dimethoxybenzaldehyde (88% yield), mp 110° C.; IR $v_{max}$ 1597, 1485, 1443, 1269, 1140, 1121, 959, 843 $cm^{-1}$; $^1$H NMR (DMSO-$d_6$) δ 8.17 (1H, dd, J=8.8, 5.4 Hz, H-4), 7.89 (1H, dd, J=10.0, 2.5 Hz, H-7), 7.64 (2H, m, H-2',6'), 7.37 (1H, td, J=9.1, 2.5 Hz, H-6), 7.15 (1H, d, J=9.0 Hz, H-5'), 3.91 (3H, s, $OCH_3$), 3.88 (3H, s, $OCH_3$); m/z (CI) 290 ($M^+$+1). Anal. ($C_{15}H_{12}NO_2SF$) C, H, N. C: found 62.34%, calc. 62.27%; H: found 4.12%, calc. 4.18%; N: found 4.76%, calc. 4.84%.

4-Fluoro-2-(3,4-dimethoxyphenyl)benzothiazole (2).

A solution of N-(2-fluorophenyl)-3,4-dimethoxythiobenzamide (0.850 g, 2.92 mmol) and sodium hydroxide (0.93 g, 23.3 mmol) in water (10 mL) and ethanol (0.5 mL) was added dropwise to a solution of potassium ferricyanide (3.84 g, 11.7 mmol) in water (5 mL) at 95° C. The resulting solution was stirred at 95° C. for a further 2 h and then cooled in an ice bath. The precipitate was collected by vacuum filtration, washed with water and dissolved in ethyl acetate (10 mL) and insoluble material was removed by filtration. The filtrate was concentrated in vacuo and the crude product purified by column chromatography (dichloromethane) to give the required product as a pale yellow powder (0.46 g, 55% yield), mp 129° C.; $^1$H NMR (DMSO-$d_6$) δ 7.95 (1H, m, ArH), 7.65 (2H, m, ArH), 7.42 (2H, m, ArH), 7.15 (1H, m, ArH), 3.90 (3H, s, OMe), 3.88 (3H, s, OMe); m/z (CI) 290 ($M^+$+1); Anal. ($C_{15}H_{12}FNO_2S$) C, H, N. C: found 62.36%, calc. 62.27%; H: found 4.19%, calc.4.18%; N: found 4.93%, calc. 4.84%.

6-Fluoro-2-(3,4-dimethoxyphenyl)benzothiazole (3).

From bis(2-amino-5-fluorophenyl)disulfide and 3,4-dimethoxybenzaldehyde (98% yield), mp 153-155° C.; $^1$H NMR (CDCl$_3$) δ7.93 (1H, dd, J=4.8, 8.8, H-4), 7.64 (1H, d, J=2.3, H-2'), 7.51 (1H, dd, J=2.3, 10.5, H-6'), 7.51 (1H, d, J=3.5, H-7), 7.18 (1H, dt, J=2.5, 9.0, H-5), 6.89 (1H, d, J=10.5, H-5'), 4.02 (3H, s, OMe), 3.96 (3H, s, OMe); m/z (CI) 290 (M$^+$+1); Anal. (C$_{15}$H$_{12}$FNO$_2$S) C, H, N. C: found 62.38%, calc. 62.27%; H: found 4.13%, calc. 4.18%; N: found 4.62%, calc. 4.84%.

5-Fluoro-2-(3-hydroxy-4-methoxyphenyl)benzothiazole (5).

From bis(2-amino-4-fluorophenyl)disulfide and 3-hydroxy-4-methoxybenzaldehyde (92% yield), mp 169-172° C.; IR $ν_{max}$ 2577, 1601, 1568, 1481, 1252, 1148, 963, 851 cm$^{-1}$; $^1$H NMR (DMSO-d$_6$) δ9.57 (1H, brs, OH), 8.15 (1H, dd, J=5.4, 8.8, H-4), 7.86 (1H, dd, J=2.2, 9.7, H-7), 7.54 (2H, m, H-2', H-6'), 7.34 (1H, td, J=2.5, 9.1, H-6), 7.10 (1H, d, J=8.0, H-5'), 3.88 (3H, s, OCH$_3$); m/z (CI) 276 (M$^+$+1). Anal. (C$_{14}$H$_{10}$NO$_2$SF.½H$_2$O) C, H, N. C: found 59.31%, calc. 59.14%; H: found 3.60%, calc. 3.90%; N: found 4.57%, calc. 4.93%.

5-Fluoro-2-(4-hydroxy-3-methoxyphenyl)benzothiazole (6).

From bis(2-amino-4-fluorophenyl)disulfide and 4-hydroxy-3-methoxybenzaldehyde (88% yield), mp 156° C.; IR $ν_{max}$ 1609, 1591, 1476, 1451, 1252, 1182, 963, 860 cm$^{-1}$; $^1$H NMR (DMSO-d$_6$) δ9.94 (1H, brs, OH), 8.14 (1H, dd, J=5.3, 8.8, H-4), 7.86 (1H, dd, J=2.4, 10.0, H-7), 7.63 (1H, d, J=2.0, H-2'), 7.52 (1H, dd, J=2.0, 8.2, H-6'), 7.33 (1H, td, J=2.5, 9.1, H-6), 6.96 (1H, d, J=8.2, H-5'), 3.91 (3H, s, OCH$_3$); m/z (CI) 276 (M$^+$+1). Anal. (C$_{14}$H$_{10}$NO$_2$SF.¼H$_2$O) C, H, N. C: found 60.12%, calc. 60.10%; H: found 3.63%, calc. 3.78%; N: found 4.83%, calc. 5.00%.

5-Fluoro-2-(3,4-methylenedioxyphenyl)benzothiazole (7).

From bis(2-amino-4-fluorophenyl)disulfide and 3,4-methylenedioxybenzaldehyde (78% yield), mp 161-164° C.; $^1$H NMR (CDCl$_3$) δ7.78 (1H, dd, J=5.2, 8.8 Hz, H-7), 7.69 (1H, dd, J=2.0, 9.6 Hz, H-6'), 7.57 (2H, m, H-2', H-4), 7.13 (1H, dt, J=2.4, 8.8 Hz, H-6), 6.90 (1H, d, J=7.6 Hz, H-5'), 6.06 (2H, s, OCH$_2$O); m/z (CI) 274 (M$^+$+1); Anal. (C$_{14}$H$_8$FNO$_2$S) C, H, N. C: found 61.67%, calc. 61.53%; H: found 2.85%, calc. 2.95%; N: found 4.97%, calc. 5.13%.

5-Fluoro-2-(3,4-dihydroxyphenyl)benzothiazole (9).

From bis(2-amino-4-fluorophenyl)disulfide and 3,4-dihydroxybenzaldehyde (13% yield), mp 197° C.; IR 3300 (O—H) cm$^{-1}$; $^1$H NMR (CDCl$_3$) 69.80 (1H, brs, OH), 9.55 (1H, brs, OH), 8.11 (1H, dd, J=5.3, 8.7 Hz, H-7), 7.82 (1H, dd, J=2.2, 9.9 Hz, H-6'), 7.52 (1H, d, J=2.0 Hz, H-5'), 7.40 (1H, dd, J=2.2, 8.2 Hz, ArH), 7.31 (1H, dt, J=2.4, 9.0 Hz, H-6).

5-Fluoro-2-(4-methoxy-3-methylphenyl)benzothiazole (22).

From bis(2-amino-4-fluorophenyl)disulfide and 4-methoxy-3-methylbenzaldehyde (50% yield), mp 120° C.; IR $ν_{max}$ 2851 cm$^{-1}$; $^1$H NMR (CDCl$_3$) δ 7.85 (2H, m, ArH), 7.76 (1H, dd, J=5.2, 8.8 Hz, H-7), 7.71 (1H, dd, J=2.4, 9.7 Hz, H-6'), 7.13 (1H, dt, J=2.5, 8.8 Hz, H-6), 6.88 (1H, d, J=9.2 Hz, H-5'), 3.89 (3H, s, OCH$_3$), 2.29 (3H, s, CH$_3$); m/z (CI) 274 (M$^+$+1);

5-Chloro-2-(3,4-dimethoxyphenyl)benzothiazole (23).

From bis(2-amino-4-chlorophenyl)disulfide[11,18] and 3,4 dimethoxybenzaldehyde (65% yield), mp 154-155° C.; $^1$H NMR (CDCl$_3$) 68.02 (1H, d, J=2.1, H-4), 7.71 (1H, d, J=8.3, H-7), 7.68 (1H, d, J=2.3, H-2'), 7.59 (1H, dd, J=2.3, 8.4, H-6'), 7.39 (1H, dd, J=2.1, 8.3, H-6), 6.97 (1H, d, J=8.4, H-5'), 4.01 (3H, s, OMe), 3.98 (3H, s, OMe); m/z (CI) 307 (M$^+$+1). Anal. (C$_{15}$H$_{12}$ClNO$_2$S) C, H, N. C: found 58.69%, calc. 58.92%; H: found 3.92%, calc. 3.96%; N: found 4.41%, calc. 4.58%.

5-Bromo-2-(3,4-dimethoxyphenyl)benzothiazole (24).

Formed, by cyclisation of ortho-bromo thiobenzanilide (51% yield), mp 157-158° C.; $^1$H NMR (CDCl$_3$) δ8.19 (1H, d, J=1.8, H-4), 7.74 (1H, d, J=8.5, H-7), 7.70 (1H, d, J=2.0, H-2'), 7.60 (1H, dd, J=2.0, 8.4, H-6'), 7.48 (1H, dd, J=1.8, 8.5, H-6), 6.96 (1H, d, J=8.4, H-5'), 4.04 (3H, s, OMe), 3.98 (3H, s, OMe); m/z (CI) 350 (M$^+$+1). Anal. (C$_{15}$H$_{12}$BrNO$_2$S) C, H, N. C: found 51.36%, calc. 51:44%; H: found 3.25%, calc. 3.45%; N: found 4.13%, calc. 4.00%.

5-Fluoro-2-(3-fluoro-4-methoxyphenyl)benzothiazole (25).

From bis(2-amino-4-fluorophenyl)disulfide and 3-fluoro-4-methoxybenzaldehyde (65% yield), mp 157-159° C.; $^1$H NMR (CDCl$_3$) δ7.84 (3H, m, H-2', H-6', H-7), 7.73 (1H, dd, J=2.5, 9.1 Hz, H-4), 7.17 (1H, dt, J=2.5, 9.1 Hz, H-6), 7.07 (1H, t, J=8.5 Hz, H-5'), 3.99 (3H, s, OMe); m/z (CI) 278 (M$^+$+1); Anal. (C$_{14}$H$_9$F$_2$NOS) C, H, N. C: found 60.26%, calc. 60.64%; H: found 3.09%, calc. 3.27%; N: found 4.88%, calc. 5.05%.

5-fluoro 2-(3-Chloro-4-methoxyphenyl)benzothiazole-(26).

From bis(2-amino-4-fluorophenyl)disulfide and 3-chloro-4-methoxybenzaldehyde (64% yield), mp 160-161° C.; $^1$H NMR (CDCl$_3$) δ8.13 (1H, d, J=2.2, H-2'), 7.94 (1H, dd, J=2.2, 8.6 Hz, H-6'), 7.81 (1H, dd, J=5.1, 8.8 Hz, H-7), 7.72 (1H, dd, J=2.5, 9.5 Hz, H-4), 7.16 (1H, dt, J=2.5, 8.8 Hz, H-6), 7.02 (1H, d, J=8.6, H-5'), 3.99 (3H, s, OMe); m/z (CI) 294 (M$^+$+1); Anal. (C$_{14}$H$_9$ClFNOS) C, H, N. C: found 57.33%, calc. 57.24%; H: found 3.02%, calc. 3.09%; N: found 4.63%, calc. 4.77%.

2-(3-Bromo-4-methoxyphenyl)-5-fluorobenzothiazole (27).

From bis(2-amino-4-fluorophenyl)disulfide and 3-bromo-4-methoxybenzaldehyde (46% yield), mp 173-175° C.; $^1$H NMR (CDCl$_3$) δ8.31 (1H, d, J=2.2, H-2'), 7.99 (1H, dd, J=2.2, 8.6, 2.2, H-6'), 7.81 (1H, dd, J=5.1, 8.8, H-7), 7.72 (1H, dd, J=2.5, 9.5, H-4), 7.16 (1H, dt, J=2.5, 8.8, H-6), 7.00 (1H, d, J=8.6, H-5'), 3.99 (3H, s, OMe); m/z (CI) 338 (M$^+$+1); Anal. (C$_{14}$H$_9$BrFNOS) C, H, N. C: found 49.37%, calc. 49.72%; H: found 2.67%, calc.2.68%; N: found 3.96%, calc. 4.14%.

5-Fluoro-2-(3-iodo-4-methoxyphenyl)benzothiazole (28).

From bis(2-amino-4-fluorophenyl)disulfide and 3-iodo-4-methoxybenzaldehyde (56% yield), mp 167° C.; $^1$H NMR (CDCl$_3$) 68.52 (1H, d, J=2.2, H-2'), 8.03 (1H, dd, J=2.2, 8.6 Hz, H-6'), 7.82 (1H, dd, J=5.1, 8.8 Hz, H-7), 7.72 (1H, dd, J=2.5, 9.5 Hz, H-4), 7.16 (1H, dt, J=2.5, 8.8, H-6), 6.92 (1H, d, J=8.6 Hz, H-5'), 3.98 (3H, s, OMe); m/z (CI) 386 (M$^+$+1); Anal. (C$_{14}$H$_9$FINOS) C, H, N. C: found 43.26%, calc. 43.65%; H: found 2.20%, calc. 2.36%; N: found 3.43%, calc. 3.60%.

5-Fluoro-2-(4-methoxyphenyl)benzothiazole (29).

From bis(2-amino-4-fluorophenyl)disulfide and 4-methoxybenzaldehyde (43% yield), mp 123-124° C.; $^1$H NMR (CDCl$_3$) δ 8.03 (2H, d, J=8.9 Hz, H-2', H-6'), 7.80 (1H, dd, J=5.1, 8.8 Hz, H-6), 7.72 (1H, dd, J=2.5, 9.6 Hz, H-4), 7.14 (1H, dt, J=2.5, 8.8 Hz, H-5), 7.01 (2H, d, J=8.9 Hz, H-3', H-5'), 3.90 (3H, s, OMe); m/z (CI) 261 (M$^+$+1); Anal. (C$_{14}$H$_{10}$FNOS) C, H, N. C: found 64.71%, calc. 64.85%; H: found 3.92%, calc. 3.89%; N: found 5.41%, calc. 5.40%.

2-(4-Hydroxyphenyl)-4-methylbenzothiazole (30)

$^1$H NMR (d$_6$-DMSO) δ 10.27 (1H, bs, OH), 7.95 (2H, d, J=8.7 Hz, H-2',6'), 7.90 (1H, dd, J=6.5, 2.7 Hz, H-7), 7.31 (2H, m, H-5,6), 6.95 (2H, d, J=8.7 Hz, H-3',5'), 2.71 (3H, s, CH$_3$)

5-Fluoro-2-(4-hydroxyphenyl)benzothiazole (31)

$^1$H NMR (d$_6$-DMSO) δ 10.31 (1H, bs, OH), 8.14 (1H, dd, J=8.8, 5.4 Hz, H-4), 7.95 (2H, d, J=8.7 Hz, H-2',6'), 7.83 (1H, dd, J=10.0, 2.5 Hz, H-7), 7.32 (1H, td, J=9.0, 2.5 Hz, H-6), 6.95 (2H, d, J=8.7 Hz, H-3',5')

5-Trifluoromethyl-2-(4-hydroxyphenyl)benzothiazole (32)

$^1$H NMR (d6-DMSO) δ 10.41 (1H, bs, OH), 8.36 (1H, d, J=8.4 Hz, H-7), 8.32 (1H, d, =0.8 Hz, H-4), 7.99 (2H, d, J=8.8 Hz, H-2',6'), 7.74 (1H, dd, J=8.4, 0.9 Hz, H-6), 6.97 (2H, d, J=8.8 Hz, H-3',56'

6-Fluoro-2-(4-hydroxyphenyl)benzothiazole (33)

$^1$H NMR (d$_6$-DMSO) δ 10.27 (bs, 1H, OH), 8.00 (2H, m, H-7, H-4), 7.92 (2H, d, J=8.7 Hz, H-2',6'), 7.38 (1H, td, J=9.1, 2.7 Hz, H-5), 6.94 (2H, d, J=8.7 Hz, H-3',5')

6-Chloro-2-(4-hydroxyphenyl)benzothiazole (34)

$^1$H NMR (d$_6$-DMSO) δ 10.31 (1H, bs, OH), 8.39 (1H, d, J=2.0 Hz, H-7), 7.94 (2H, d, J=8.7 Hz, H-2',6'), 7.92 (1H, d, J=8.7 Hz, H-4), 7.65 (1H, dd, J=8.7, 2.0 Hz, H-5), 6.95 (2H, d, J=8.7 Hz, H-3',5')

6-Bromo-2-(4-hydroxyphenyl)benzothiazole (35)

$^1$H NMR (d6-DMSO) δ 10.33 (1H, bs, OH), 8.27 (1H, d, J=2.2 Hz, H-7), 7.98 (1H, d, J=8.7 Hz, H-4), 7.94 (2H, d, J=8.3 Hz, H-2',6'), 7.54 (1H, dd, J=8.7, 2.2 Hz, H-5), 6.95 (2H, d, J=8.4 Hz, H-3',5')

6-Ethyl-2-(4-hydroxyphenyl)benzothiazole (36)

$^1$H NMR (d$_6$-DMSO) δ 10.30 (1H, bs, OH), 7.90 (4H, m, H-4,7,2',6'), 7.36 (1H, dd, J=8.4, 1.5 Hz, H-5), 6.94 (2H, d, J=8.6 Hz, H-3',5'), 2.75 (2H, q, J=7.5 Hz, CH$_2$),1.26 (3H, t, J 7.5 Hz, CH$_3$)

2-(4-Hydroxyphenyl)-6-methoxybenzothiazole (37)

$^1$H NMR (d$_6$-DMSO) δ 10.17 (1H, bs, OH), 7.87 (3H, m, H-4,2',6'), 7.68 (1H, d, J=2.6 Hz, H-2), 7.10 (1H, dd, J=2.6, 8.9 Hz, H-5), 6.92 (2H, d, J=8.7 Hz, H-3 ',5'), 3.84 (3H, s, OCH$_3$)

6-Ethoxy-2-(4-hydroxyphenyl)benzothiazole (38)

$^1$H NMR (d$_6$-DMSO) δ 10.23 (1H, bs, OH), 7.88 (2H, d, J=8.7 Hz, H-2',6'), 7.86 (1H, d, J=8.9 Hz, H-4), 7.66 (1H, d, J=2.5 Hz, H-7), 7.08 (1H, dd, J=8.9, 2.6 Hz, H-5), 6.92 (2H, d, J=8.7 Hz, H-3',5'), 4.12 (2H, q, J=6.9 Hz, CH$_2$), 1.38 (3H, t, J=6.9 Hz, CH$_3$)

2-(4-Hydroxyphenyl)-6-methylsulfonylbenzothiazole (39)

$^1$H NMR (d$_6$-DMSO) δ 10.51 (1H, bs, OH), 8.77 (1H, d, J=1.4 Hz, H-7), 8.19 (1H, d, J=8.6 Hz, H-4), 8.02 (2H, d, J=8.7 Hz, H-2',6'), 7.62 (1H, m, H-5), 6.97 (2H, d, J=8.7 Hz, H-3',5'), 3.31 (3H, S, SO$_2$CH$_3$)

2-(4-Hydroxyphenyl)-5,6-dimethylbenzothiazole (40)

$^1$H NMR (d$_6$-DMSO) δ 10.18 (1H, bs, OH), 7.90 (2H, d, J=10.0 Hz, H-2',6'), 7.82 (1H, s, H-4/7), 7.78 (in, s, H-4/7), 6.94 (2H, d, J=10.0 Hz, H-3',5'), 2.37 (3H, s, CH$_3$), 2.36 (3H, s, CH$_3$)

5-Fluoro-2-(3-hydroxyphenyl)benzothiazole (41)

$^1$H NMR (d$_6$-DMSO) δ 9.95 (1H, bs, OH), 8.20 (1H, dd, J=8.9, 5.4 Hz, H-4), 7.93 (1H, dd, J=9.9, 2.5 Hz, H-7), 7.53 (2H, m, phenyl-H), 7.39 (2H, m, phenyl-H), 7.00 (1H, td, J=9.5, 2.3 Hz, H-6)

5-Fluoro-2-(3,5-dimethoxyphenyl)benzothiazole (42).

From bis(2-amino-4-fluorophenyl)disulfide and 3,5-dimethoxybenzaldehyde (75% yield), mp 115° C.; $^1$H NMR (CDCl$_3$) δ 7.82 (1H, dd, J=8.8, 5.1 Hz, H-7), 7.75 (1H, dd, J=9.5, 2.4 Hz, H-4), 7.24 (2H, d, J=2.3 Hz, H-2', 6'), 7.17 (1H, dt, J=8.8, 2.5 Hz, H-6), 6.61 (1H, t, J2.3 Hz, H-4'), 3.90 (6H, s, 3'-OMe, 5'-OMe); IR ν$_{max}$ 1601, 1458, 1350, 1273, 1126, 1065, 966, 820 cm$^{-1}$; m/z (CI) 290 (M$^+$+1). Anal. (C$_{15}$H$_{12}$NO$_2$SF.H$_2$O) C, H, N. C: found 59.02%, calc. 58.62%; H: found 4.39%, calc. 4.59%; N: found 4.16%, calc. 4.56%.

5-Fluoro-2-(3,4,5-trimethoxyphenyl)benzothiazole (43).

From bis(2-amino-4-fluorophenyl)disulfide and 3,4,5-trimethoxybenzaldehyde (77% yield), mp 120-122° C.; $^1$H NMR (CDCl$_3$) δ 7.83 (1H, dd, J=8.8, 5.1 Hz, H-7), 7.75 (1H, dd, J=9.6, 2.5 Hz, H-4),7.32 (2H, s, H-2', 6'), 7.17 (1H, dt, J=8.8, 2.5 Hz, H-6),4.00 (6H, s, 3'-OMe, 5'-OMe), 3.94 (3H, s, 4'-OMe); m/z (CI) 320 (M$^+$+1). Anal. (C$_{16}$H$_{14}$FNO$_3$S) C, H, N. C: found 60.22%, calc. 60.18%; H: found 4.42%, calc. 4.42%; N: found 4.24%, calc. 4.39%.

5-Fluoro-2-(3-methoxy-4-methoxymethyloxyphenyl)benzothiazole (44).

From bis(2-amino-4-fluorophenyl)disulfide and 3-methoxy-4-methoxymethyloxybenzaldehyde (35% yield), mp 101-102° C.; $^1$H NMR (DMSO-d$_6$) δ 8.18 (1H, dd, J=8.8, 5.4 Hz, H-7), 7.91 (1H, dd, J=9.9, 2.5 Hz, H-4), 7.69 (1H, d, J=2.1 Hz, H-2'), 7.62 (1H, dd, J=8.4, 2.1 Hz, H-6'), 7.37 (1H, dt, J=9.0, 2.5 Hz, H-6), 7.26 (1H, d, J=8.4 Hz, H-5'), 5.30 (2H, s, OCH$_2$OCH$_3$), 3.93 (3H, s, OCH$_3$), 3.43 (3H, s, OCH$_2$OCH$_3$); m/z (CI) 320 (M$^+$+1). Anal. (C$_{16}$H$_{14}$FNO$_3$S) C, H, N. C: found 59.58%, calc. 60.18%; H: found 4.37%, calc. 4.42%; N: found 4.21%, calc. 4.39%.

2-(3-Ethoxy-4-methoxyphenyl)-5-fluorobenzothiazole (45).

From bis(2-amino-4-fluorophenyl)disulfide and 3-ethoxy-4-methoxybenzaldehyde (41% yield), mp 136-139° C.; $^1$H NMR (CDCl$_3$) δ 7.82 (1H, dd, J=8.8, 5.1 Hz, H-7), 7.73 (2H, m, H-2', H-4), 7.59 (1H, dd, J=8.4, 2.1 Hz, H-6'), 7.16 (1H, dt, J=8.8, 2.5 Hz, H-6), 6.97 (1H, d, J=8.4 Hz, H-5'), 4.21 (2H, q, J=7.0 Hz, OCH$_2$CH$_3$), 4.04 (3H, s, OCH$_3$), 1.55 (3H, t, J=7.0 Hz, OCH$_2$CH$_3$); m/z (CI) 304 (M$^+$+1). Anal. (C$_{16}$H$_{14}$FNO$_2$S) C, H, N. C: found 63.22%, calc. 63.35%; H: found 4.60%, calc. 4.65%; N: found 4.56%, calc.4.62%.

2-(3,4-Diethoxyphenyl)-5-fluorobenzothiazole (46).

From bis(2-amino-4-fluorophenyl)disulfide and 3,4-diethoxybenzaldehyde (59% yield), mp 109-113° C.; $^1$H NMR (CDCl$_3$) δ 7.80 (1H, dd, J=8.7, 5.1 Hz, H-7), 7.71 (2H, m, H-2', H-4), 7.57 (1H, dd, J=8.4, 2.1 Hz, H-6'), 7.14 (1H, dt, J=8.8, 2.5 Hz, H-6), 6.95 (1H, d, J=8.4 Hz, H-5'), 4.22 (4H, m, 3'-OCH$_2$CH$_3$, 4'-OCH$_2$CH$_3$), d 1.56-1.50 (6H, m, 3'-OCH$_2$CH$_3$, 4'-OCH$_2$CH$_3$); m/z (CI) 318 (M$^+$+1). Anal. (C$_{17}$H$_{16}$FNO$_2$S) C, H, N. C: found 64.12%, calc. 64.33%; H: found 5.19%, calc. 5.08%; N: found 4.39%, calc. 4.41%.

2-(2, 3, 4-Trimethoxyphenyl)-5-fluorobenzothiazole (50)

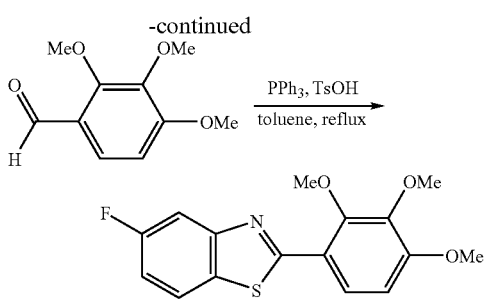

91% yield; mp 109-110° C.; $^1$H NMR (DMSO-$d_6$) δ 8.16 (2H, dd+dd, H-7, H-6'), 7.86 (1H, dd, J=10.0, 2.5 Hz, H-4), 7.34 (1H, dt, J=9.0, 2.5 Hz, H-6), 7.08 (1H, d, J=9.1 Hz, H-5'), 4.04 (3H, s, OMe), 3.95 (3H, s, OMe), 3.86 (3H, s, OMe); MS (CI) 320 (M+); Anal. ($C_{16}H_{14}FNO_3S$) C,H,N. C: found 60.04%, calc. 60.18%; H: found 4.29%, calc. 4.42%; N: found 4.30%, calc. 4.39%.

Synthesis of 5-fluoro-2-(3-bromopropyloxy-4-methoxyphenyl)benzothiazole (51)

To a solution of 5-fluoro-2-(3-hydroxy-4-methoxyphenyl) benzothiazole 5 (0.15 g, 0.55 mmol) in $CH_3CN$ (30 ml) were added $K_2CO_3$ (0.11 g, 0.82 mmol) and 1,3-dibromopropane (0.28 ml, 2.74 mmol), and the mixture was heated under reflux at 80° C. for 24 hours. The reaction mixture was allowed to cool at room temperature and then concentrated in vacuum. The residue was taken up with $CHCl_3$ (30 ml), and the $CHCl_3$ layer was washed with 0.2N NaOH aq (30 ml×2), then dried and concentrated in vacuum. The residue was purified by column chromatography on silica gel (chloroform), followed by recrystallisation from ethanol/water to give a white solid.

Yield 12% (0.027 g), 14%; mp 95-98° C.; IR 2959, 1594 (C=N) $cm^{-1}$; $^1$H NMR δ 7.80(1H, dd, J=5.11, 8.77 Hz, H-7), 7.71 (2H, m, H-2', H-6'), 7.61 (1H, dd, J=2.10, 8.40 Hz, H-4), 7.14 (1H, td, J=2.49, 8.78 Hz, H-6), 6.96 (1H, d, J=8.42 Hz, H-5'), 4.31 (2H, t, J=5.91 Hz, $CH_2$a), 3.95 (3H, s, $CH_3$), 3.68 (2H, t, J=6.43 Hz, $CH_2$c), 2.44 (2H, t, J=6.18 Hz, $CH_2$b); MS m/z 398.00 (M+1). Anal. ($C_{17}H_{15}FNSO_2Br$) C, H, N.

Synthesis of 5-fluoro-2-(3-morpholinopropyloxy-4-methoxyphenyl)benzothiazole (52)

To a solution of morpholine (0.080 ml, 0.91 mmol) in $CH_3CN$ (10 ml) were added $K_2CO_3$ (0.13 g, 0.96 mmol) and 5-fluoro-2-(3-bromopropyloxy-4-methoxyphenyl)benzothiazole 51 (0.36 g, 0.91 mmol), and the mixture was heated under reflux at 80° C. for 16 hours. The reaction mixture was allowed to cool at room temperature and then concentrated in vacuum. The residue was partitioned between $CHCl_3$ (30 ml×2) and $H_2O$ (40 ml), then the $CHCl_3$ layer was dried and concentrated in vacuum. The residue was purified by recrystallisation (ethanol) to give the free base as a pale cream solid.

Yield 25% (0.091 g); mp 95-98° C.; IR 2957, 2863, 2810, 1595 (C=N) $cm^{-1}$; $^1$H NMR δ 7.82 (1H, dd, J=5.20, 8.80 HZ, H-7), 7.73 (2H, m, H-2', H-6'), 7.60 (1H, dd, J=2.00, 8.40 Hz, H-4), 7.16 (1H, td, J=2.40, 8.80 Hz, H-6), 6.97 (1H, d, J=8.40 Hz, H-5'), 4.26 (2H, t, J=6.80 Hz, $CH_2$a), 3.97 (3H, s, $CH_3$), 3.76 (4H, t, J=4.40 Hz, H-e), 2.59 (2H, t, J=7.20 Hz, $CH_2$c), 2.51 (4H, br, H-d), 2.11 (2H, t, J=7.20 Hz, $CH_2$b); MS m/z 403.14 (M+1).

General Methods for the Synthesis of Esters.

Method C Phenol (5) or (6) were reacted with an excess of acid chloride in pyridine at 25° C. for two hours. Excess water was then added to the reaction mixture and the precipitate collected by filtration following by further washing with water. The crude product was purified recrystallised from $MeOH/H_2O$.

Method D Phenol (5) or (6) were reacted with acid chloride (1.1 equiv.) in $CH_2Cl_2$ containing triethylamine (2 equiv) and DMAP (0.2 equiv) at reflux for 48 hours. The solution was then washed with 1M HCl and then concentrated in vacuo. The crude product was recrystallised from $MeOH/H_2O$. The following compounds were prepared:

2-(3-Acetoxy-4-methoxyphenyl)-5-fluorobenzothiazole (11).

From 5 and acetyl chloride via Method D (40%), mp 190° C.; IR 2850, 1757 (C=O) $cm^{-1}$; $^1$H NMR ($CDCl_3$) δ 7.89 (1H, dd, J=2.2, 8.6 Hz, ArH), 7.81 (2H, m, ArH), 7.69 (1H, dd, J=2.2, 9.6 Hz, ArH), 7.13 (1H, dt, J=2.5, 8.8 Hz H-6), 7.04 (1H, d, J=8.6 Hz, H-5') 3.90 (3H, s, OMe), 2.38 (3H, s, COMe); m/z (CI) 318 (M$^+$+1); Anal. ($C_{16}H_{12}FNO_3S$) C, H, N. C: found 60.39%, calc.60.56%; H: found 3.81%, calc. 3.81%; N: found 4.26%, calc. 4.41%.

2-(3-Ethanoyloxy-4-methoxyphenyl)-5-fluorobenzothiazole (12)

$^1$H NMR ($CDCl_3$) δ 7.89 (1H, dd, J=8.6, 2.2 Hz, H-7), 7.81 (2H, m, ArH), 7.69 (1H, dd, J=9.6, 2.4 Hz, ArH), 7.13 (1H, dt, J=8.8, 2.5 Hz, H-6), 7.04 (1H, d, J=8.6 Hz, H-5'), 3.90 (3H, s, OMe), 2.65 (2H, q, J=7.3 Hz, $\underline{CH_2}CH_3$), 1.30 (3H, t, J=7.3 Hz, $CH_3CH_2$)

5-Fluoro-2-(3-propionyloxy-4-methoxyphenyl)benzothiazole (13).

From 5 and propionyl chloride via Method C (30%), mp 150° C.; IR 2851, 1759 (C=O) $cm^{-1}$; $^1$H NMR ($CDCl_3$) δ 7.89 (1H, dd, J=2.2, 8.6 Hz, H-7), 7.81 (2H, m, ArH), 7.69 (1H, dd, J=2.2, 9.6 Hz, ArH), 7.13 (1H, dt, J=2.5, 8.8 Hz, H-6), 7.04 (1H, d, J=8.6 Hz, H-5') 3.90 (3H, s, OMe), 2.65 (2H, q, J=7.3 Hz, $CH_2$), 1.30 (3H, t, J=7.3, $\underline{H_3}CH_2$); m/z (CI) 332 (M$^+$+1); Anal. ($C_{17}H_{14}FNO_3S$) C, H, N. C: found 61.26%, calc. 61.62%; H: found 4.14%, calc. 4.26%; N: found 4.09%, calc. 4.23%.

2-(3-Benzoyloxy-4-methoxyphenyl)-5-fluorobenzothiazole (14).

From 5 and benzoyl chloride via Method C (87%), mp 160° C.; IR 2849, 1733 (C=O) $cm^{-1}$; $^1$H NMR ($CDCl_3$) δ 8.24 (2H, dd, J=1.5, 8.2 Hz, ArH), 7.97 (2H, m, ArH), 7.80 (1H, dd, J=5.1, 8.8 Hz, ArH), 7.69 (2H, m, ArH), 7.55 (2H, m, ArH), 7.14 (1 H, dt, J=2.5, 8.8 Hz, H-6), 7.10 (1H, d, J=8.5 Hz, H-5') 3.91 (3H, s, OMe); m/z (CI) 380 (M$^+$+1); Anal. ($C_{21}H_{14}FNO_3S$) C, H, N. C: found 66.17%, calc. 66.48%; H: found 3.71%, calc. 3.72%; N: found 3.55%, calc. 3.69%.

2-[3-(2-Chlorobenzoyloxy)-4-methoxyphenyl]-5-fluorobenzothiazole (15).

From 5 and 2-chlorobenzoyl chloride via Method C (82%), mp 190° C.; IR 2849, 1740 (C=O) $cm^{-1}$; $^1$H NMR ($CDCl_3$) δ 8.15 (1H, dd, J=1.3, 7.0 Hz, H-7), 7.97 (2H, m, ArH), 7.81 (1H, dd, J=5.1, 8.8 Hz, ArH), 7.71 (1H, d, J=2.5, 9.6 Hz, ArH), 7.55 (2H, m, ArH), 7.43 (1H, m, ArH), 7.14 (1H, dd, J=2.5, 8.8 Hz, H-6), 7.12 (1H, d, J=8.3 Hz, ArH) 3.94 (3H, s, OMe); m/z (CI) 414 (M$^+$+1); Anal. ($C_{21}H_{13}ClFNO_3S$) C, H, N. C: found 60.67%, calc. 60.95%; H: found 3.08%, calc. 3.17%; N: found 3.04%, calc. 3.38%.

2-[3-(2-Bromobenzoyloxy)-4-methoxyphenyl]-5-fluorobenzothiazole (16).

From 5 and 2-bromobenzoyl chloride via Method C (85%), mp 220-223° C.; IR 2851, 1740 (C=O), 550 cm$^{-1}$; $^1$H NMR (CDCl$_3$) δ 8.41 (1H, m, ArH), 8.19 (1H, m, ArH), 7.99 (1H, m, ArH), 7.95 (1H, m, ArH), 7.83 (2H, m, ArH), 7.72 (1H, m, ArH), 7.45 (1H, m, ArH), 7.16 (2H, m, ArH), 3.94 (3H, s, OMe). m/z (CI) 458 (M$^+$+1);

5-Fluoro-2-[3-(3-nitrobenzoyloxy)-4-methoxyphenyl]benzothiazole (17).

From 5 and 3-nitrobenzoyl chloride via Method C (80%), mp 212° C.; IR 2850, 1749 (C=O) cm$^{-1}$; $^1$H NMR (CDCl$_3$) δ 9.21 (1H, m, ArH), 8.68 (2H, m, ArH), 8.12 (1H, m, ArH), 7.90 (3H, m, ArH), 7.39 (1H, m, ArH), 7.30 (1H, m, ArH), 4.05 (3H, s, OMe); m/z (CI) 425 (M$^+$+1); Anal. (C$_{21}$H$_{13}$FN$_2$O$_5$S) C, H, N. C: found 59.25%, calc. 59.43%; H: found 2.95%, calc. 3.09%; N: found 6.38%, calc. 6.60%.

5-Fluoro-2-[3-(4-nitrobenzoyloxy)-4-methoxyphenyl]benzothiazole (18).

From 5 and 4-nitrobenzoyl chloride via Method C (81%), mp 198° C.; IR 2851, 1745 (C=O) cm$^{-1}$; $^1$H NMR (CDCl$_3$) δ 8.58 (4H, m, ArH), 8.17 (2H, m, ArH), 7.90 (2H, m, ArH), 7.42 (2H, m, ArH), 4.10 (3H, s, OMe); m/z (CI) 425 (M$^+$+1); Anal. (C$_{12}$H$_{13}$FN$_2$O$_5$S) C, H, N. C: found 59.78%, calc. 59.43%; H: found 3.04%, calc. 3.09%; N: found 6.40%, calc. 6.60%.

5-Fluoro-2-[3-(morpholin-4-ylcarbonyloxy)-4-methoxyphenyl]benzothiazole (19).

From 5 and morpholin-4-ylcarbonyl chloride via Method C (90%), mp 170° C.; IR 2860, 1712 (C=O) cm$^{-1}$; $^1$H NMR (CDCl$_3$) δ 7.92 (1H, m, ArH), 7.85 (1H, m, ArH), 7.80 (1H, m, ArH), 7.70 (1H, m, ArH), 7.27 (1H, m, ArH), 7.14 (1H, m, ArH), 7.06 (1H, m, ArH), 3.94 (3H, s, OMe), 3.65 (8H, m, 4×CH$_2$); m/z (CI) 389 (M$^+$+1); Anal. (C$_{19}$H$_{17}$FN$_2$O$_4$S) C, H, N. C: found 58.36%, calc. 58.75%; H: found 4.49%, calc. 4.41%; N: found 7.27%, calc. 7.21%.

5-Fluoro-2-[4-(morpholin-4-ylcarbonyloxy)-3-methoxyphenyl]benzothiazole (20).

From 6 and morpholin-4-ylcarbonyl chloride via Method C (75%), mp 126° C.; IR 2867, 1722 (C=O) cm$^{-1}$; $^1$H NMR (CDCl$_3$) δ 7.80 (3H, m, ArH), 7.58 (1H, m, ArH), 7.20 (2H, m, ArH), 3.98 (3H, s, OMe), 3.71 (8H, m, 4×CH$_2$); m/z (CI) 389 (M$^+$+1); Anal. (C$_{19}$H$_{17}$FN$_2$O$_4$S) C, H, N. C: found 58.48%, calc. 58.75%; H: found 4.42%, calc. 4.41%; N: found 7.24%, calc. 7.21%.

5-Fluoro-2-[4-(3-nitrobenzoyloxy)-3-methoxyphenyl]benzothiazole (21).

From 6 and 3-nitrobenzoyl chloride via Method C (27%), mp 190° C.; IR 2849, 1745 (C=O) cm$^{-1}$; $^1$H NMR (CDCl$_3$) δ 9.08 (1H, dt, J=2.0, 9.1 Hz, ArH), 8.54 (2H, m, ArH), 7.85 (2H, m, ArH), 7.75 (2H, m, ArH), 7.66 (1H, dd, J=2.0, 8.2 Hz, ArH), 7.30 (1H, d, J=8.2 Hz, ArH), 7.19 (1H, dt, J=2.5, 8.8 Hz, ArH), 3.98 (3H, s, OMe); m/z (CI) 425 (M$^+$+1); Anal. (C$_{21}$H$_{13}$FN$_2$O$_5$S) C, H, N. C: found 59.84%, calc. 59.43%; H: found 3.06%, calc. 3.09%; N: found 6.66%, calc. 6.60%.

2-(3-Butyroyloxy-4-methoxyphenyl)-5-fluorobenzothiazole (47).

From 5 and butyroyl chloride via Method C (75%), mp 125° C.; IR 2851, 1759 (C=O) cm$^{-1}$; $^1$H NMR (CDCl$_3$) δ 7.89 (1H, dd, J=2.2, 8.6 Hz, H-7), 7.81 (2H, m, ArH), 7.69 (1H, dd, J=2.4, 9.6 Hz, ArH), 7.13 (1H, dt, J=2.5, 8.8 Hz, H-6), 7.04 (1H, d, J=8.6 Hz, H-5') 3.90 (3H, s, OMe), 2.60 (2H, t, J=7.3 Hz, COC$\underline{H}_2$CH$_2$), 1.82 (2H, sext, J=7.3 Hz, CH$_2$C$\underline{H}_2$CH$_3$), 1.30 (3H, t, J=7.3, C$\underline{H}_3$CH$_2$); m/z (CI) 346 (M$^+$+1); Anal. (C$_{18}$H$_{16}$FNO$_3$S) C, H, N. C: found 62.44%, calc. 62.59%; H: found 4.65%, calc. 4.67%; N: found 3.73%, calc. 4.06%.

5-Fluoro-2-(4-methoxy-3-(3-nitrobenzoyl)oxyphenyl)benzothiazole (49)

From 6
$^1$H NMR (CDCl$_3$) δ 9.08 (1H, t, J=2.0 Hz, ArH), 8.54 (2H, m, ArH), 7.85 (2H, m, ArH), 7.75 (2H, m, ArH), 7.66 (1H, dd, J=8.2, 2.0 Hz, ArH), 7.30 (1H, d, J=8.2 Hz, ArH), 7.19 (1H, dt, J=8.8, 2.5 Hz, ArH), 3.98 (3H, s, OMe)

Synthesis of N-oxide Derivatives 2-(3,4-Dimethoxyphenyl)-5-fluorobenzothiazole N-oxide (53)

To a solution of 2-(3,4-dimethoxyphenyl)-5-fluorobenzothiazole (1.31 g. 4.53 mmol) and maleic anhydride (1.0 g, 10.2 mmol) in dichloromethane (20 mL) was added 30% aq. hydrogen peroxide (1 mL, 8.8 mmol) dropwise with stirring. The mixture was heated under reflux for 12 h, then the mixture allowed to cool (ice-water bath), and the precipated maleic acid by-product removed by filtration. The filtrate was concentrated in vacuo and purified by column chromatography on neutral alumina using dichloromethane as eluant, to give the product N-oxide, which was rerystallised from methanol, 10% yield, mp 201.4° C., $^1$H NMR (CDCl$_3$), δ 8.58 (1H, d, J=2.1 Hz, H-2'), δ 7.81 (1H, dd, J=2.5, 8.7 Hz, H-7), δ 7.73 (1H, dd, J=2.1, 8.6 Hz, H-6'), δ 7.63 (1H, dd, J=4.5, 8.7 Hz, H-4), δ 7.21 (1H, dt, J=2.5, 8.7 Hz, H-6), δ 6.89 (1H, d, J=8.6 Hz, H-5'), δ 3.94 (3H, s, OCH$_3$), δ 3.89 (3H, s, OCH$_3$). Anal. calcd for C$_{15}$H$_{12}$FNO$_3$S (MW 305.32).

2-(3,4-Dimethoxyphenyl)benzothiazole N-oxide (54)

Following the same procedure as for the synthesis of 2-(3,4-Dimethoxyphenyl)-5-fluorobenzothiazole N-oxide, described above, gave the N-oxide product, which was recrystallised from methanol, yield 20%, $^1$H NMR (CDCl$_3$), δ 8.72 (1H, d, J=2.1 Hz, H-2'), δ 8.19 (1H, d, J=7.9 Hz, H-7), δ 7.81 (1H, dd, J=2.1, 8.3 Hz, H-6'), δ 7.75 (1H, d, J=7.9 Hz, H-4), δ 7.61 (1H, dt, J=1.1, 7.9 Hz, H-6), δ 7.53 (1H, dt, J=1.1, 7.9 Hz, H-5), δ 6.97 (1H, d, J=8.3 Hz, H-5'), δ 4.02 (3H, s, OCH$_3$), δ 3.96 (3H, s, OCH$_3$). Anal. calcd for C$_{15}$H$_{12}$FNO$_3$S (MW 287.33).

It is of course to be understood that the present invention is described by way of example only and is not intended to be restricted to the foregoing examples, and embodiments.

References (1) Loaiza-Pérez, A. L.; Trapani, V.; Hose, C.; Singh, S. S.; Trepel, J.; Stevens, M. F. G.; Bradshaw, T. D.; Sausville, E. A. The aryl hydrocarbon receptor mediates sensitivity of MCF-7 breast cancer cells to the antitumor agent 2-(4-amino-3-methylphenyl)benzothiazole. *Mol. Pharmacol.* 2002, 61, 13-19; Trapani, V.; Patel, V.; Ciolino, H. P.; Yeh, G. C.; Hose, C.; Trepel, J. B.; Stevens, M. F. G.; Sausville, E. A.; Loaiza-Pérez, A. L. DNA damage and cell cycle arrest induced by 2-(4-amino-3-methylphenyl)-5-fluorobenzothiazole (5F 203, NSC 703786) is attenuated in aryl hydrocarbon receptor deficient MCF-7 cells. *Br. J. Cancer* 2003, 88, 599-605.

(2) Leong, C. O.; Suggitt, M.; Swaine, D. J.; Bibby, M. C.; Stevens, M. F. G.; Bradshaw, T. D. In vitro, in vivo, and in silico analyses of the antitumor activity of 2-(4-amino-3-methylphenyl)-5-fluorobenzothiazoles. *Mol. Cancer Ther.* 2004, 3, 1565-1575.

(3) Chang, Y.-H.; Peak, J. D.; Wierschke, S. W.; Feld, W. A. A general and efficient synthesis of 2-phenylbenzothiazoles from diphenyl disulfides. *Synth. Comm.* 1993, 23, 663-670.

(4) Hutchinson, I.; Chau, M-Z.; Browne, H. L.; Trapani, V.; Bradshaw, T. D.; Westwell, A. D.; Stevens, M. F. G. Antitumor benzothiazoles. 14. Synthesis and in vitro biological properties of fluorinated 2-(4-amino-phenyl) benzothiazoles. *J. Med. Chem.* 2001, 44, 1445-1455.

(5) Shi, D-F.; Bradshaw, T. D.; Wrigley, S.; McCall, C. J.; Lelieveld, P.; Fichtner, I.; Stevens, M. F. G. Antitumor benzothiazoles. 3. Synthesis of 2-(4-aminophenyl)benzothiazoles and evaluation of their activities against breast cancer cell lines in vitro and in vivo. *J. Med. Chem.* 1996, 39, 3375-3384.

(6) Hutchinson, I.; Stevens, M. F. G.; Westwell, A. D. The regiospecific synthesis of 5- and 7-monosubstituted and 5,6-disubstituted 2-arylbenzothiazoles. *Tetrahedron Lett.* 2000, 41, 425-428.

(7) Boyd, M. R.; Paull, K. D. Some practical considerations and applications of the National Cancer Institute in vitro anticancer drug discovery screen. *Drug Dev. Res.* 1995, 34, 91-104.

(8) Ranu, B. C.; Jana, R.; Dey, S. S. An efficient and green synthesis of 2-arylbenzothiazoles in an ionic liquid, [pmIm]Br under microwave irradiation. *Chem. Lett.* 2004, 33, 274-275.

(9) Chakraborti, A. K.; Rudrawar, S.; Kaur, G.; Sharma, L. An efficient conversion of phenolic esters to benzothiazoles under mild and virtually neutral conditions. *Synlett,* 2004, 1533-1536.

The invention claimed is:

1. A compound of general structure I, wherein the compound is optionally in the form of an N-oxide or S-oxide or prodrug form and/or pharmaceutically acceptable salt thereof wherein:

$R^1$ is independently selected from hydrogen, fluorine, and $^{18}F$ isotope;

$R^2$ is independently selected from hydrogen, fluorine, and $^{18}F$ isotope;

$R^3$ is independently selected from hydrogen, fluorine, and $^{18}F$ isotope;

$R^4$ is independently selected from hydrogen, fluorine, and $^{18}F$ isotope;

$R^5$ is hydrogen;

$R^6$ is methoxy;

$R^7$ is methoxy;

$R^8$ is hydrogen;

$R^9$ is hydrogen; with the proviso that only one of $R^1$-$R^4$ is always fluorine.

2. A compound of claim 1, wherein at least one of $R^1$ to $R^4$ is an $^{18}F$ isotope.

3. A method of using the compounds of claim 1 in Positron Emission Tomography imaging comprising the steps of:

(a) preparing $^{18}F$ radiolabeled compounds of claim 1 which bear a fluoro substituent;

(b) administering said $^{18}F$ radiolabeled compound of claim 1 to a patient who may benefit from Positron Emission Tomography imaging; and (c) tracing the $^{18}F$ radiolabeled compound of claim 1 through the body of the patient using Positron Emission Tomography imaging techniques.

4. A pharmaceutical composition comprising a therapeutically effective amount of a compound of claim 1.

5. A compound according to claim 1 wherein $R^1$, $R^3$ and $R^4$ are each hydrogen and $R^2$ is fluorine.

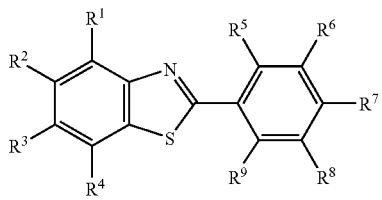

I

* * * * *